United States Patent
Bonello et al.

(10) Patent No.: US 7,071,378 B1
(45) Date of Patent: Jul. 4, 2006

(54) PLANT SEED ENDOSPERM SPECIFIC PROMOTER

(75) Inventors: Jean-Francois Bonello, Bussy St Georges (FR); Peter Rogowsky, Lyons (FR); Pascual Perez, Chanonat (FR)

(73) Assignees: Biogemma, Paris (FR); Centre National de la Recherche Scientifique (C.N.R.S.), Paris (FR)

( * ) Notice: Subject to any disclaimer, the term of this patent is extended or adjusted under 35 U.S.C. 154(b) by 398 days.

(21) Appl. No.: 10/089,612

(22) PCT Filed: Sep. 19, 2000

(86) PCT No.: PCT/FR00/02596

§ 371 (c)(1),
(2), (4) Date: Sep. 18, 2002

(87) PCT Pub. No.: WO01/25439

PCT Pub. Date: Apr. 12, 2001

(30) Foreign Application Priority Data

Oct. 1, 1999 (FR) .................................. 99 12305

(51) Int. Cl.
*C12N 15/82* (2006.01)
*A01H 5/00* (2006.01)
*A01H 5/08* (2006.01)
*A01H 5/10* (2006.01)

(52) U.S. Cl. ...................... 800/287; 536/24.1; 800/298; 800/320; 800/306; 800/320.1; 800/320.3; 800/322; 435/320.1; 435/419

(58) Field of Classification Search ................ 800/295, 800/298, 320, 306, 320.1, 320.3, 322, 287; 435/320.1, 419; 536/23.1, 24.1
See application file for complete search history.

(56) References Cited

FOREIGN PATENT DOCUMENTS

| | | |
|---|---|---|
| EP | 0 412 006 | 2/1991 |
| WO | WO 91/09957 | 7/1991 |
| WO | WO 93/09237 | 5/1993 |
| WO | WO 97/28247 | 8/1997 |
| WO | WO 98/08961 | 3/1998 |
| WO | WO 98/10062 | 3/1998 |
| WO | WO 98/26064 | 6/1998 |
| WO | WO 99/40209 | 8/1999 |

OTHER PUBLICATIONS

Opsahl-Ferstad HG et al. ZmEsr, a novel endosperm-specific gene expressed in a restricted region around the maize embryo. Plant J. Jul. 1997;12(1):235-46.*
Czako et al. Mol Gen Genet 1992. vol. 235, pp. 33-40 (IDS).*
Gunn et al. The Plant Journal. 1997. vol. 12(1), pp. 235-246 (IDS).*
Kim et al. Plant Mol Biol 1994. vol. 24, pp. 105-117.*
Fiedler U. et al. A complex ensemble of cis-regulatory elements controls the expression of a *Vicia faba* non-storage seed protein gene. Plant Mol Biol. Jul. 1993;22(4):669-79.*
H.-G. Opsahl-Ferstad et al., "ZmEsr, a novel endosperm-specific gene expressed in a restricted region around the maize embryo", vol. 12, No. 1, 1997, pp. 235-246.
J.-F. Bonello et al., "Esr genes show different levels of expression in the same region of maize endosperm", vol. 246, 2000, pp. 219-227.
M. Czako et al., "Differential manifestation of seed mortality induced by seed-specific expression of the gene for diphtheria toxin A chain in *Arabidopsis* and tobacco", vol. 235, Jan. 1, 1992, pp. 33-40.

* cited by examiner

*Primary Examiner*—Cynthia Collins
(74) *Attorney, Agent, or Firm*—Young & Thompson

(57) ABSTRACT

The invention concerns promoter nucleotide sequences enabling expression of encoding sequences whereto they can be bound, which is specific of the endosperm region enclosing the embryo of seeds of Angiosperms and which intervene in particular in the early stages of endosperm development, and their use for agronomic or nutritional improvement of plants.

14 Claims, 11 Drawing Sheets

FIG.9

→ Repeat CTACACC in tandem
— Repeat TTTTA --→ Repeat ATTCT

Promoter or Es.z gene
Codified sequence for Esr2 gene
Terminator Ca MV 35 S

SEQUENCE LISTING

```
<160> NUMBER OF SEQ ID NOS: 22

<210> SEQ ID NO 1
<211> LENGTH: 531
<212> TYPE: DNA
<213> ORGANISM: Zea mays

<400> SEQUENCE: 1
gatcattaag gactaagcag tcttttcccc tttcggcttg catcatcttt agtcttcatc     60
```

-continued

| | |
|---|---|
| actattataa gccgaagcta ttaccccttg gctatagctt cggtgttcat ctttattatc | 120 |
| ttcggactat gtcttcacct tgtataccttt tgtcttgggg gaaaaccttc atcctgaagc | 180 |
| cgaagctccc tgtaataatt catatcatgc taaaaataaa tggtcagtcc tgttttttgag | 240 |
| gaccttcgga agaggaaggc cccccaacaa gacgattaac tagtattgtc tcactgcatt | 300 |
| gtttttttgg cacttcatca ataatgcctc aatagcatac ttcattttag gaactttatt | 360 |
| aaaactgtct taaaatagggg ccaagtcata aattcattca aagtgactct tcatttctta | 420 |
| cttcctatct ttggtggttt tgtatatata tatgttcatg gttgagtgat gttcctacac | 480 |
| cactacacca cacgttagat atatatacag aaaatagctt cactatctag a | 531 |

<210> SEQ ID NO 2
<211> LENGTH: 2493
<212> TYPE: DNA
<213> ORGANISM: Zea mays

<400> SEQUENCE: 2

| | |
|---|---|
| aagcttttcc ggtgatgaag cacctgtaat acttaacagc atgctgaaaa caaatagtta | 60 |
| gctgtgtttt tgaggacctt cggaagatga aggcccccaa cacatcccat gcatcaagtc | 120 |
| cccatgactt gcaaaaaagc aaattttatc aaaatttctc ataaaacact tgaaaacatt | 180 |
| tctcttttg aaaagtgtag agcactagca actgtctact aaaaaggttc ccaaatttct | 240 |
| gggtataaca atcgcatggt aaataacaca aaggaaatcc tactaagagc agtaatttgg | 300 |
| ctaaaacaat agtgagcatt ttaatgtaat agggaatagg agcatgcaat acttgtgttc | 360 |
| tttcagggtt ttgatgtcct caaaagtgtg cccccctggg gcagttgcaa cactcaaaat | 420 |
| ctactcgtat acataaagaa acatgggcac aaaataagaa acaatactca aattatgaaa | 480 |
| aaggttcaaa tggtcctata attattgtag acattttaga atttatttta gaccaaaacc | 540 |
| atttaaattt ggttttaaaat gagttagata ttaatattta ttcagttat agttatttgg | 600 |
| gacatttatt tacttaacta taacttctag ggttttaaaa gtaaattttg ggtccctagt | 660 |
| tggaactagc tcagattgct ggttgatttc cataaaagtc gaggttcctt tagcaaaaat | 720 |
| ccacggtgaa caaggggggag ataggtgttg accgatatct ctaaattttg atcgttggac | 780 |
| ggcacatgga tgtctcagat taaatggtgg atgtgcaagc gacgcgcaca cgatggagga | 840 |
| atggcttcac gacggtgggc tactagagct ggctacgtca accaatggag ggctcggtca | 900 |
| aggtcaaaat ttgttgccaa gccactgtgg ctcacgatga gtcgattgag cacatatcaa | 960 |
| ggtcgagggt caaccagagg ggcaagatcg atggtgcagt ggtgttctcg atggaagggg | 1020 |
| aaacttcggt gagcaattca agatttccta tcatgtgacc gggtcaggga atgggcgcat | 1080 |
| ggggtttggt accttctggt gcacatcatg ttgctgtatc gatgtcaagg gagcattagg | 1140 |
| gttcacgagt cagcgatgac gggcatggtg ggacttgtgt caccatggtt cgatcaacta | 1200 |
| gggacgatag agctctatga agtttcacaa cttcctcaca ctctagggat catggtgaca | 1260 |
| aaggtgggga ggacggggcg tctctagtga gggtggaatg cagttctgtc acgtgggaat | 1320 |
| agtggcggca tcgcttgtaa tgaataaaag gtgcttgggt ggctgggaag tgcaatatga | 1380 |
| gggaagtagt tggtgcgggg atgttccttt tataagggag caccattgat taatggaaga | 1440 |
| caatgacaca aagggtggtg cgacagttta agctcgaat gctgctaggg gtgctcaagg | 1500 |
| ttaaaagatc aggcatcagg gaggaaaggc agggataaaa tttctttact ccagttgtgg | 1560 |
| ggtgatgggg acaagggtag tgctcaagca agggagggcg agttcagcgc agagatgcct | 1620 |
| gttgtgacac atggggggggg gggaattgga ggttggggtt gaccaggtga cgttatggcg | 1680 |

-continued

```
tgacccagag aagagaccca ctgatgggga aaaaaggtgc aacaggtgg ggaccaaggt    1740 gtcagtgact caccgtgaca tgttattgga agttacgtc cggaatggtt tgggcctgag    1800
tgatctaggc tggctcgggc actgtgctga tcctttaatt tctccattcc caatttaagt    1860 tgaatttta attcaaatca aatgactcca aatctctcca aaattaccaa aatatagaat    1920
atttagatga atatgttggt ggagtttggg ctccgctttt ggttagtatg tttgtataaa    1980
aataatttct ctccttttgt cacttccaat attgacttaa attttatgt agcaatgcca    2040 acttttttta gtagtgtgcc acttatagca caaaaactat atccattttc taatagtcct    2100
tgaaatccac attctatttt tagccattct tcaaaattgg cacaaaacta ggaaaattta    2160
atacattctt gccataacat attcagtgc aatgttaac tagattgctc aatattagca    2220
aacttctttt gtaagattca ttaatattgc tacattgcat acttttttag aagttcatca    2280
ataatgcctc attagcatac ttcattttag gaacttgatt aaaaccgcct taaaatagag    2340
ccaagtgacg gatccattta aaggtgattc ttaatttctt acttcctatc tttggtggct    2400 tatgttttata tatgtgtggg tggttgaatg atgttcctac accactacac cacacgttgg    2460
acatatatat ggaaaatagc ttcacagtct aga    2493
```

<210> SEQ ID NO 3
<211> LENGTH: 1708
<212> TYPE: DNA
<213> ORGANISM: Zea mays

<400> SEQUENCE: 3

```
aagcttagaa atttaaaaa agccaggca agcgttggtg tgcaaagagc taaaaattag     60
gaagacaaga gaacacggca agaaagcatg ctaaatgtgc tcgcggtgcg ttcttattta    120
tacgctcaat acgttgcaag tggtagggcc ccacttgtca ttgactattg ctattctagc    180
aaagggaagg tgtttttcgg accttcggct taaggcctc gtccatatcg caatctgaat    240
ttatcattct aacaaattaa tattgtgagg ggctactgtt gggggccttc gacttccgaa    300
ggtcctcaaa aactggttta acagtgtttc tggagtataa tgcataaaca ggtatcttcg    360
ggtttggatc agaactacaa catgaagagg cacaaagaac acgaaggttg gcgcagagcc    420
gaagctcacg tgtaggagag cttcggcacg acagcagaaa aagggaaccg acttaaaagg    480
aaaggctatt cagacctcga tggatttcta taggtcatta gcaaatgtaa agggcatgaa    540 tgtaattta catgggctgt gtccttgcct ataaatagat gaacagtact ctcgtactgt    600
tcacgctgac ttggcattcg cttttttgcat cacgcttgta cccttgctttt ccttcaaacc    660 gaaggtacat ctataattg ttattgtgtt attgtggata tggtaatgca aataaaaata    720
agttgatgat aatgtttata ttatttttcg tatttcatat atgaattctt cctcatcatt    780
tattgtgctt acgaaggttt ttccttcaaa atctttgtcc ggaattcatt atatccgaag    840
ggaaataatg tctcgaagga cgaaggactt tgatatttaa cactttttcat gttgccttgt    900 tcttgactct tagcatttga gaacaagtcc ccaacagctc ctaagctctt ctttgaagaa    960
acaactacta gatgaagttt ctccaaaagt acgtccattg aatggagtaa agagtcattt   1020
gacctctcgg aataaaatta aaatgagaat agtaagaat aaaacacctc tattatcaaa   1080
tctaggccat acaaacattg ggtattacta aaaaatagct aatgccatct ttcaacattt   1140
ggaagttaaa accaaccaat cctcactcat tcccagaaaa tattggatca tatttaacat   1200
tttgtgtcac ttacaaaaat ggcttaatct tttatgcggc aatgccaacc ttttttagca   1260
```

-continued

| | |
|---|---|
| gggtgccact tgtaacatga aaactataac tattttcaaa tagtaccttg aaattcgcat | 1320 |
| tctatttta tgcattcttc aaaattgaca caaattaaac taggagaatt caatacattc | 1380 |
| ttgccataac atattctaat gcaaatatta agtagattgc tcaacatcgg tacacatctt | 1440 |
| ttggacgatt aattagtatt gtctcactac attctttgtt ttagcagttc atcaataatg | 1500 |
| cctcaatagc atacttcatt taggaactt tatgaaaatt gtcttaaaat agggccaagt | 1560 |
| cacaaatcca cttcaaaggt gactcttcat ttcttacttc ctatctttgc ttgtttttgt | 1620 |
| atatatatgt gtggatggtt gagtgatgtt cctacaccac tacaccacac cttagacaca | 1680 |
| tatatgaaaa atagcttcac tgtctaga | 1708 |

<210> SEQ ID NO 4
<211> LENGTH: 1232
<212> TYPE: DNA
<213> ORGANISM: Zea mays

<400> SEQUENCE: 4

| | |
|---|---|
| tagttcatgc aaaagtagtg agtgtttata cacctatgcc aatgaataac ctctaactac | 60 |
| cctcatgtac tggcctggtg tttggtaaac atgaagcaat aatttcctct tatcaaaata | 120 |
| cgggtctcaa gctgcatgtg aaaaataata atatttttt tgaagtgaat gaaaaatgat | 180 |
| aaatatgaaa cagtaaatct ttccgttgaa aaagtacatc tctattatta acgataaacct | 240 |
| atatatcaat ctacaatgcg ctcatctgca tctcgatgca tactttcatc attttatgaa | 300 |
| tgtactttaa tgataagaag gattagaatg ttccttgtttt cctcttattc ttacctttt | 360 |
| caaaattatc agtttccaat gtctgaatat gcaatgcatt ataaaccta gtcagcatat | 420 |
| atcaagtcga tatataatgc tatatgttta agaactggtg ctgagtatgt ctactcaaca | 480 |
| tatttttag ctattggatc gagcagttta gtaaaggtaa actacattta tctatcttca | 540 |
| agttgtattt tcccacccctt aaattatgaa agggagtaac gctccactcc aactgttgaa | 600 |
| agggaacaaa tttggtctcc ggactgattt cattggtggt tctctatttt ttaaaacaac | 660 |
| aaaaaaacat atttgttctc tgaaaattga taattaatta atcataaatt aggaaaaaaa | 720 |
| ctatatgaaa ctagttatag ttttcttcta aaattattgt ctgtctgttg gtgctctagt | 780 |
| tatagagtta taacatgaaa actatagcca ttttcaaata gtgccttgaa attcatttt | 840 |
| gtttagccat tcttcaaaat tgccaccaaa ccaggagaat ttattaataa attcacgcca | 900 |
| taacatattc tagtccaaat gttaagtgga ttgctcaata tcattatact tcttttggac | 960 |
| gattcattag tactgccttg ttgcatactt tgttttagca gttcatcaat aatgcttcac | 1020 |
| tagcataatt catgttagga acttgattaa aactgccttta agaacatggc aaagtgataa | 1080 |
| atccacttca aaggcaatta ttaatttctt acttcctatc ttttggtggtt tttgtatata | 1140 |
| tgtgtgtggg tggttgagtg atgcacacat tttcctacac cactacatca caccttggac | 1200 |
| atatatgtga aaaatagct tcgcagtcta ga | 1232 |

<210> SEQ ID NO 5
<211> LENGTH: 499
<212> TYPE: DNA
<213> ORGANISM: Zea mays

<400> SEQUENCE: 5

| | |
|---|---|
| ttttgtcact tccaatattg acttaaattt ttatgtagca atgccaactt tttttagtag | 60 |
| tgtgccactt atagcacaaa aactatatcc attttctaat agtccttgaa atccacattc | 120 |
| tatttttagc cattcttcaa aattggcaca aaactaggaa aatttaatac attcttgcca | 180 |

```
taacatattc tagtgcaaat gttaactaga ttgctcaata ttagcaaact tcttttgtaa    240
gattcattaa tattgctaca ttgcatactt ttttagaagt tcatcaataa tgcctcatta    300
gcatacttca ttttaggaac ttgattaaaa ccgccttaaa atagagccaa gtgacggatc    360
catttaaagg tgattcttaa tttcttactt cctatctttg gtggcttatg tttatatatg    420
tgtgggtggt tgaatgatgt tcctacacca ctacaccaca cgttggacat atatatggaa    480
aatagcttca cagtctaga                                                 499

<210> SEQ ID NO 6
<211> LENGTH: 507
<212> TYPE: DNA
<213> ORGANISM: Zea mays

<400> SEQUENCE: 6
ttgtgtcact tacaaaaatg gcttaatctt ttatgcggca atgccaacct tttttagcag     60
ggtgccactt gtaacatgaa actataact attttcaaat agtaccttga aattcgcatt    120
ctatttttat gcattcttca aaattgacac aaattaaact aggagaattc aatacattct    180
tgccataaca tattctaatg caaatattaa gtagattgct caacatcggt acacatcttt    240
tggacgatta attagtattg tctcactaca ttctttgttt tagcagttca tcaataatgc    300
ctcaatagca tacttcattt taggaacttt atgaaaattg tcttaaaata gggccaagtc    360
acaaatccac ttcaaaggtg actcttcatt tcttacttcc tatctttgct tgttttgta     420 tatatatgtg tggatggttg agtgatgttc ctacaccact acaccacacc ttagacacat    480
atatggaaaa tagcttcact gtctaga                                        507

<210> SEQ ID NO 7
<211> LENGTH: 265
<212> TYPE: DNA
<213> ORGANISM: Zea mays
<220> FEATURE:
<221> NAME/KEY: modified_base
<222> LOCATION: (1)
<223> OTHER INFORMATION: a, c, t, g, other or unknown
<220> FEATURE:
<221> NAME/KEY: modified_base
<222> LOCATION: (32)
<223> OTHER INFORMATION: a, c, t, g, other or unknown
<220> FEATURE:
<221> NAME/KEY: modified_base
<222> LOCATION: (35)
<223> OTHER INFORMATION: a, c, t, g, other or unknown
<220> FEATURE:
<221> NAME/KEY: modified_base
<222> LOCATION: (128)
<223> OTHER INFORMATION: a, c, t, g, other or unknown
<220> FEATURE:
<221> NAME/KEY: modified_base
<222> LOCATION: (136)
<223> OTHER INFORMATION: a, c, t, g, other or unknown
<220> FEATURE:
<221> NAME/KEY: modified_base
<222> LOCATION: (175)
<223> OTHER INFORMATION: a, c, t, g, other or unknown

<400> SEQUENCE: 7
namgattmay tartattgyy wcaytrcatw snttnttttr gmasttcatc aataatgcct     60
cawtagcata cttcatttta ggaacttkat kaaaayygyc ttaaaatagr gccaagtsay    120
rratycantt yaaagntgay tcttmatttc ttacttccta tctttgstkg yttwngtwta    180
tatatrtgtk srtggttgar tgatgttcct acaccactac accacacstt rgayayatat    240
```

```
ayrgaaaata gcttcacwrt ctaga                                          265
```

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 8

```
ggggtctaga ctgtgaagct attttcca                                        28
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 9

```
ggggaagctt tacattcttg ccataacata                                      30
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 10

```
ggggaagctt ttcatcaata atgcctcatt                                      30
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 11

```
ggggaagctt taatttctta cttcctatct                                      30
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 12

```
ggccagtcga caaagcggcc gcatgca                                         27
```

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 13

```
tcagctgttt cgccggcgt                                                  19
```

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgactgcag ccca                                                         14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcttgggct gcag                                                         14

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctagacccga attcgc                                                       16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggccgcgaat tcgggt                                                       16

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatccactag tcccg                                                        15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aattcgggac tagtg                                                        15

```
<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagctttttg cggccgc                                                    17

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tcgagcggcc gcaaaaagct tagct                                           25

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctagattcc atg                                                        13
```

PLANT SEED ENDOSPERM SPECIFIC PROMOTER

The present invention relates to controlling the expression of genes during the development of the endosperm. It concerns in particular promoter nucleotide sequences which enable expression which is both specific to the interface between the embryo and the endosperm and early during the development of the endosperm.

The endosperm, a characteristic formation of Angiosperm seeds, is a nutritive tissue for the embryo. This is a tissue which is complex in its structure and development, in particular with cereals. The central area of the endosperm consists of large cells with vacuoles, which store the reserves of starch and proteins, whilst the region surrounding the embryo is distinguished by rather small cells, occupied for the major part by cytoplasm. At the present time the function of these cells, referred to as "dense cytoplasmic cells" (Schel et al. 1984) is not known. In 1994 Opsahl et al. identified a gene expressed specifically in this small region around the maize embryo, a gene which they called Esr standing for "Embryo Surrounding Region".

The authors of the present invention have now isolated promoter nucleotide sequences enabling an expression of the coding sequences with which they can be bound, which is specific to the region of the endosperm surrounding the embryo in Angiosperm seeds and which intervenes particularly in the early stages of the development of the endosperm.

Such promoter sequences are particularly useful for targeting or regulating the expression of genes of interest.

In the context of an improvement to plants by transgenesis, a promoter nucleotide sequence of this type can be bound effectively to a coding sequence for a gene of interest.

The nucleotide construction, preferably inserted in a vector, can be used for transforming plant cells in a stable fashion, so that the plant thus transformed contains in its genome the gene of interest associated with the promoter sequence of the invention.

The seeds which grow, by fertilisation, from this plant also contain this transgene in their genome.

Because of its association with the promoter sequence of the invention, this transgene of interest will be expressed only in the region of the endosperm surrounding the embryo, that is to say in the dense cytoplasmic cells as mentioned above.

The expression of the transgene begins from the very first days after pollination, more precisely as from the fourth day after pollination.

The promoter sequences of invention can advantageously be selected from the group consisting of the sequence comprising the sequences SEQ ID NO: 1, NO: 2, NO: 3, NO: 4, NO: 5, NO: 6 or NO: 7 and any nucleotide sequence which is a homologue of these.

The sequence SEQ ID NO: 1 corresponds to the gene promoter Esr1.

The sequence SEQ ID NO: 2 corresponds to the gene promoter Esr2.

The sequence SEQ ID NO: 3 corresponds to the gene promoter Esr3.

The sequence SEQ ID NO: 4 corresponds to the gene promoter Esr4.

The sequence SEQ ID NO: 5 corresponds to a fragment of 499 pairs of bases on SEQ ID NO: 2 (nucleotides 1995–2493).

The sequence SEQ ID NO: 6 corresponds to a fragment of 507 pairs of bases on SEQ ID NO: 3 (nucleotides 1202–1708).

The sequence SEQ ID NO: 7 is a consensus sequence of 265 nucleotides, obtained by means of comparison between the sequences SEQ ID NO: 1, NO: 2 and NO: 3.

"Homologous nucleotide sequence" means any nucleotide sequence which differs from the sequence SEQ ID NO: 1, NO: 2, NO: 3, NO: 4, NO: 5, NO: 6 or NO: 7, by a substitution, deletion and/or insertion of one or more nucleotides, at positions such that these homologous nucleotide sequences preserve the property of specific promoter of the sequences SEQ ID NO: 1 to NO: 7.

Preferably such a homologous nucleotide sequence is identical to at least 70% of the sequences SEQ ID NO: 1 to NO: 7, preferably at least 80%, preferably still at least 95%.

Homology is generally determined using a sequence analysis software (for example, the Sequence Analysis Software package of the Genetics Computer Group, University of Wisconsin Biotechnology Center, 1710 University Avenue, Madison, Wis. 53705). Similar nucleotide sequences are aligned in order to obtain the maximum degree of homology (i.e. identity). To this end, it may be necessary to artificially introduce gaps in the sequence. Once the optimum alignment has been achieved, the degree of homology (i.e. identity) is established by recording all the positions for which the nucleotides of the two compared sequences are identical, with respect to the total number of positions.

Preferentially, such homologous nucleotide sequences specifically hybridises to the sequences which are complementary to the sequences SEQ ID NO: 1 to NO: 7 under stringent conditions. The parameters defining the stringency conditions depend on the temperature at which 50% of the paired strands separate (Tm).

For sequences comprising more than 30 bases, Tm is defined by the equation: Tm=81.5+0.41 (% G+C)+16.6 Log (concentration in cations)−0.63 (% formamide)−(600/number of bases) (Sambrook et al., Molecular Cloning, A Laboratory Manual, Coldspring Harbor Laboratory Press, 1989, pages 9.54–9.62).

For sequences with a length less than 30 bases, Tm is defined by the equation: Tm=4(G+C)+2(A+T).

Under appropriate stringency conditions, to which the aspecific sequences do not hybridise, the hybridisation temperature is approximately 5° to 30° C., preferably 5° to 10° C. below Tm, and the hybridisation buffers used are preferably solutions with a ionic strength such as a 6×SSC solution for example.

The various nucleotide sequences of the invention can be of artificial origin or not. They may be DNA sequences obtained by sieving banks of sequences by means of sensors produced on the basis of the SEQ ID NO: 1 to NO: 7. Such banks can be prepared by conventional techniques of molecular biology, known to persons skilled in the art.

The nucleotide sequences according to the invention can also be prepared by chemical synthesis, or by mixed methods including the chemical or enzymatic modification of sequences obtained by sieving banks.

The promoter nucleotide sequences of the invention are preferably sequences isolated from cereals, in particular maize.

The promoter nucleotide sequences according to the present invention can in particular be isolated by methods of reversed PCR or working on the genome (Devic et al., 1997).

The promoter nucleotide sequences of the invention can also comprise or be associated with a cis CTACACCA regulating pattern, preferably repeated in tandem, or any other pattern comprising one or more degenerated bases having the same function.

Another object of the present invention is a nucleotide construction, referred to as an expression cassette, comprising a promoter nucleotide sequence as defined above operatively bound to at least one gene of interest.

The said gene of interest can also be associated with other regulating elements such as activators and transcription termination sequences (terminators). By way of example of a terminator which can be used in such constructions, it is possible to cite the end 3' of the gene of nopaline synthase of *Agrobacterium tumefaciens*.

The said gene of interest can for example code for a protein involved in the development of the embryo and/or of the endosperm, cell growth, the metabolism of sugars (invertase) and fatty acids and the flow of nutrients (transporters). It can also code for a toxic protein, or for a protein activating or inhibiting other genes, such as a protein inhibiting a transcription factor (repression fields of the engrailed type (Poole et al. 1985) or co-repressors for example).

According to a preferred mode, the gene of interest codes for a protein whose specific expression in the area surrounding the embryo will make it possible to act on the size of the embryo and/or its development. By way of example, this gene can code for a barnase or isopentenyl-transferase.

The gene of interest can be placed in sense or antisense orientation.

The promoter nucleotide sequence of the invention can also be associated with a marker gene, for example a gene making it possible to select a plant transformed from a plant which does not contain transfected foreign DNA. As a marker gene, it is possible to cite in particular a gene confirming resistance to an antibiotic (Herrera-Estrella et al., EMBO J. 2, 987–995 (1983)) or resistance to a herbicide (EP 242 246).

Another object of the invention is any nucleotide vector, such as a plasmid, which can be used for transforming host cells, characterised in that it comprises an expression cassette as defined above. The construction of expression vectors for the transformation is within the capability of one skilled in the art following standard techniques.

Another object of the invention is an Angiosperm plant host cell, notably a cereal, transformed by a vector according to the invention.

The invention also concerns a transgenic plant or part of a transgenic plant, in particular seed, fruit or pollen, generated from such a cell.

Amongst the cells able to be transformed according to the method of the invention, examples are cells of extensively farmed plants (maize, wheat, rape, sunflower, peas, soya, barley, etc.) or food plants and flowers. Preferentially, it is possible to choose plants known to contain large reserves (protein, glucidic and lipidic), in particular cereal plants and oily plants.

The hybrid plants obtained by crossing plants according to the invention also form part of the invention.

Another object of the invention is a method of obtaining an Angiosperm plant having improved agronomic or nutritional qualities, comprising the steps consisting of:
transforming at least one Angiosperm plant cell by means of a vector as defined previously;
cultivating the cell thus transformed so as to generate a plant containing in its genome an expression cassette according to the invention.

The transformation of vegetable cells can be achieved by the techniques known to one skilled in the art.

It is possible to cite in particular the methods of direct transfer of genes such as direct micro-injection into plant embryoids (Neuhaus et coll. 1997), vacuum infiltration (Bechtold et al. 1993) or electroporation (Chupeau et coll., 1989) or direct precipitation by means of PEG (Schocher et coll., 1986) or the bombardment by gun of particles covered with the plasmidic DNA of interest (Fromm M et al., 1990).

It is also possible to infect the plant with a bacterial strain, in particular *Agrobacterium*. According to one embodiment of the method of the invention, the vegetable cells are transformed by a vector according to the invention, the said cell host being able to infect the said vegetable cells by allowing the integration, in the genome of the latter, of the nucleotide sequences of interest initially contained in the above-mentioned vector genome. Advantageously, the above-mentioned cell host used is *Agrobacterium tumefaciens*, in particular according to the method described in the article by An et al., (1986), or *Agrobacterium rhizogene*, in particular according to the method described in the article by Guerche et al. (1987).

For example, the transformation of vegetable cells can be achieved by the transfer of the T region of the tumour-inducing extra-chromosome circular plasmid of *Agrobacterium tumefaciens*, using a binary system (Watson et al., 1994). To do this, two vectors are constructed. In one of these vectors the T region has been eliminated by deletion, with exception of the right and left borders, a marker gene being inserted between them to allow selection in the plant cells. The other partner of the binary system is an auxiliary plasmid Ti, a modified plasmid which no longer has any T region but still contains the virulence genes vir necessary to the transformation of the vegetable cell.

According to a preferred mode, it is possible to use the method described by Ishida et al. (1996) for the transformation of Monocotyledons.

According to another protocol, the transformation is achieved according to the method described by Finer et al. (1992) using the tungsten or gold particle gun.

Another object in the invention is the use of the promoter nucleotide sequences referred to previously in molecular constructions intended to improve the agronomic, food or industrial quality of a plant, by acting in particular on the size of the embryo or of the endosperm and/or its development.

This is because an early specific action on the development of the tissues of the embryo and of the endosperm can be sought: according to the relative size of one or other tissue, it would be possible to obtain seeds or fruits with a higher starch (large endosperm) and/or oil (large embryo) content, via the use respectively of stimulator genes (hormone of the cellular cycle for example) or inhibitor genes (toxic protein or transcription inhibitor for example). Endosperms without embryos could also be obtained according to this model, for industrial applications in starch making and semolina processing.

By way of example, the use of genes coding for hormones (cytokinins, auxins) of the cell cycle, under the control of the promoters described according to the invention, would make it possible to modify the processes of cellularisation and, in a correlated fashion, the development of the endosperm in the light of the work of R J Scott (1998).

Action on the accumulation of nutrients in the embryo and endosperm can also be sought, using for example, as genes of interest, genes coding for transporters of nutrients (sugar in particular), to the interfaces between mother plant/endosperm and endosperm/embryo, or genes coding for inhibitors of these transports, for a differential accumulation of nutrients in the endosperm or embryo.

The invention therefore also relates to methods for modifying the agronomic and/or nutritional qualities of a plant, through an early targeted action on the development of the embryo/endosperm, using the transformation of the plants with a vector according to the invention. In particular, it is concerned with the modification of the size and/or the development of the embryo/endosperm. It also relates to the alteration of the development of the embryo, with a view to producing seeds without embryos for cereals in particular, presenting an interest for the starch and semolina industries.

The object of the invention is more precisely the use of an expression cassette as defined previously, for obtaining a transgenic Angiosperm plant exhibiting improved agronomic or nutritional qualities.

Advantageously, the transgenic plant obtained can produce grains with starch or oil contents which are modified in comparison with a non-transformed plant.

The invention also concerns the use of the transgenic plants obtained according to the invention, or parts of these plants in particular seeds, grains and fruits for preparing derived products, in particular food products.

The products obtained, whether it be seeds with a higher oil content, flours of seeds or grains with a higher starch or oil content, also come within the scope of the invention.

Finally, the object of the invention is any composition for human or animal food prepared from the said products obtained.

The following figures and examples illustrate the invention without limiting its scope.

LEGEND TO THE FIGURES

FIG. 9 shows a comparison of the sequences of the promoters of the genes Esr1, Esr2 and Esr3 (respectively prEsr1, prEsr2 and prEsr3, or residues 271 to 531 of SEQ ID NO: 1, residues 1992 to 2493 of SEQ ID NO: 2 and residues 1199 to 1708 of SEQ ID NO: 3), the preserved parts being aligned.

EXAMPLES

Example 1

Quantitative Expression Esr1, 2, 3

The work by Opsahl-Ferstad et al. (1997) identified by "differential display" a specific amplicon of the endosperm Esra1 (access number on the EMBL database: X98495) and isolated by screening complementary genome banks on hybrid line HD5*HD7 (Barloy et coll. 1989) and line A188 (Gerdes and Tracey, 1993) respectively, of the corresponding clones. From genome sequences Esr1 g1 (access number on EMBL: X98497) and Esr2g1 (access number on EMBL: X98499) and Esr3g2 (access number on EMBL: X99970) in particular, 3 genes Esr1, Esr2 and Esr3 were revealed.

The authors of the present invention assessed the relative contributions of expression of each of the genes Esr by means of RT-PCR experiments, digestion by restriction enzymes and quantification according to the methods known to persons skilled in the art, using DAP 7 and DAP 9 (day after pollination) equipment.

Quantification of the different bands identified on migration gel reveals relative contributions of 18%, 53% and 29% on average, for the transcripts of Esr1, Esr2 and Esr3 respectively. The promoter of Esr2 therefore affords the strongest quantitative expression of the gene which it controls.

Example 2

Isolation and Cloning of the Promoter Sequences

Figure 1:
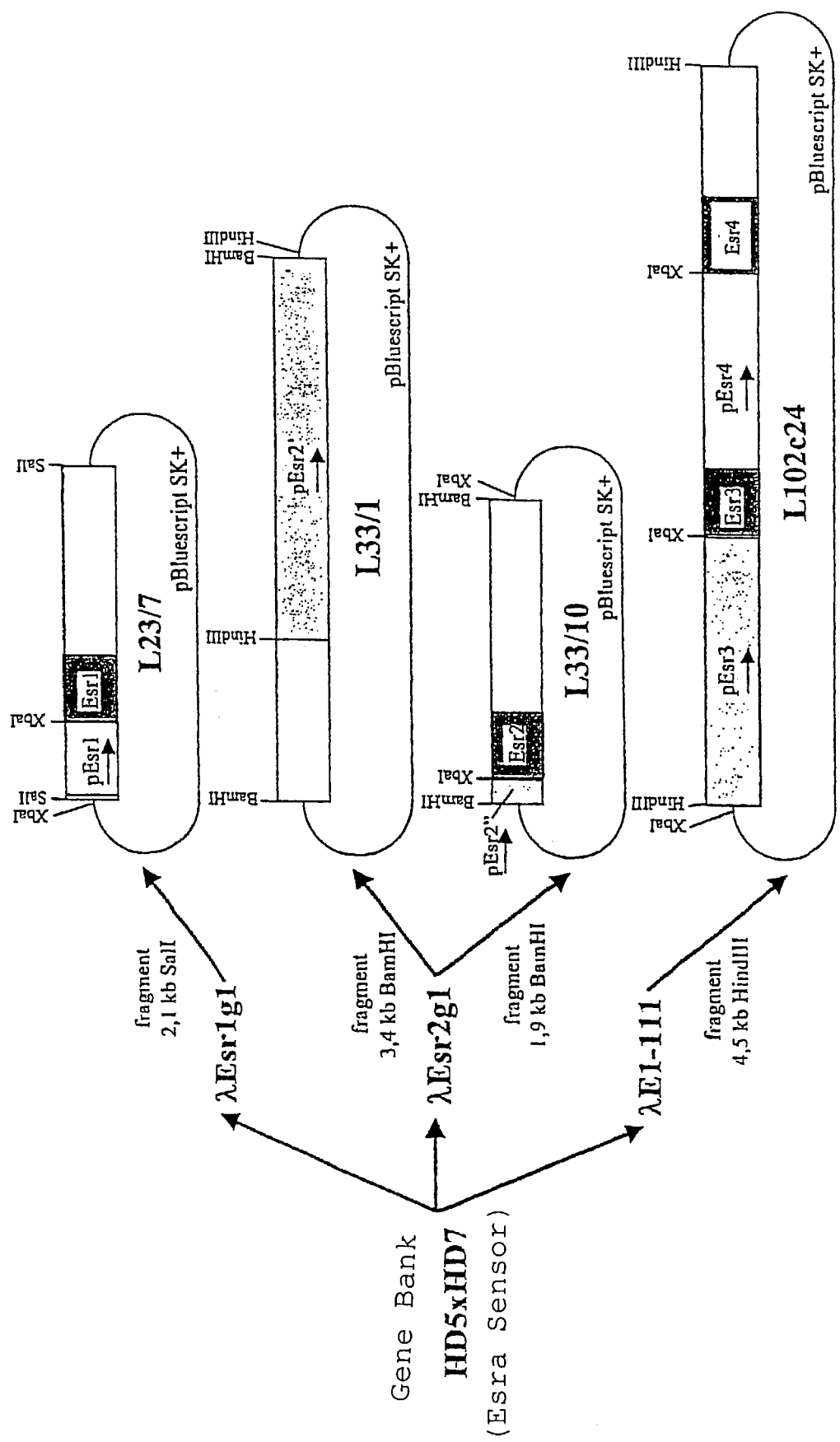
FIG. 1 depicts a diagram illustrating the steps of the cloning of the Esr promoters.

As illustrated in FIG. 1, fragments containing the open reading phases of Esr1, Esr2, and Esr3 (Opsahl et al., 1997) as well as upstream and downstream sequences were subcloned in the plasmid pBluescript SK+ (Stratagene) in accordance with the methods described in Sambrook et al. (1989). The result was the plasmid L23/7 containing a fragment SalI of 2.1 kb of λEsr1g1 and the plasmid L33/1 containing a fragment BamHI of 3.4 kb of λEsr2g1. The plasmid L33/10 containing a fragment BamHI of 1.9 kb of λEsr2g1 and the plasmid L102c24 containing a fragment HindIII of 4.5 kb of λE1-111. XbaI sites situated just upstream of the open reading phase (<u>TCTAGATTCCATG</u>) (SEQ ID NO: 22) made it possible to differentiate the putative promoters of the respective open reading phases. In particular, the fragment SalI/XbaI of 0.53 kb of L23/7 was designated as a putative promoter of Esr1, the fragment HindIII/BamHI of 2.35 kb of L33/1 (upstream part of the promoter) and the fragment BamHI/XbaI of 0.14 kb of L33/10 (downstream part of the promoter), that of the putative promoter of Esr2, the fragment HindIII/XbaI of 1.71 kb, that of the putative promoter of Esr3 and the fragment XbaI/XbaI of 1.62 kb comprising the putative promoter of Esr4. A functional promoter Esr2 of 2.49 kb was reconstructed from the fragment HindIII/BamHI of 2.35 kb of L33/1 and from the fragment BamHI/XbaI of 0.14 kb of L33/10, in a base plasmid of the pBSSK+ type (Stratagene). The orientation of the arrows in FIG. 1 represents the orientation 5'–3'.

Example 3

Structure of the Sequences Upstream of the Esr Genes

Comparisons between the sequences of the regions 5' showed two types of homologies: a highly preserved sequence which corresponds to a proximal sequence of 265 pairs of bases and sequences of retrotransposons in the distal part. As the sequences of retrotransposons are in different orientations and positions in the three promoters, they do not seem to fulfil a role in the expression of the Esr genes. Consequently, the 265 pairs of bases will contain all the cis information necessary for an expression of specific genes of the region surrounding the embryo.

The consensus sequence (SEQ ID NO: 7) was obtained after alignment of the three promoter nucleotide sequences and using Sequencher 3.1 software from Genes Codes Corporation (Ann Arbor, Mich. 48106).

The degenerated bases are described in the Nomenclature Committee of the International Union of Biochemistry (1985): Nomenclature for Incomplete Specified Bases in Nucleic Acid Sequences, European Journal of Biochemistry 150: 1–5.

In particular,
B=C, G or T but not A
D=A, G or T but not C
H=A, C or T but not G
K=G or T
M=A or C
N=G, A or C
R=G or A
S=C or G
V=A, C or G but not T
W=A or T
X=G, A, T or C
and Y=C or T.

A homology is also observed between the proximal regions which extend over approximately 500 pairs of bases between the promoter of Esr2 and that of Esr3, as defined by the sequences SEQ ID NO: 5 and NO: 6.

Figure 9:
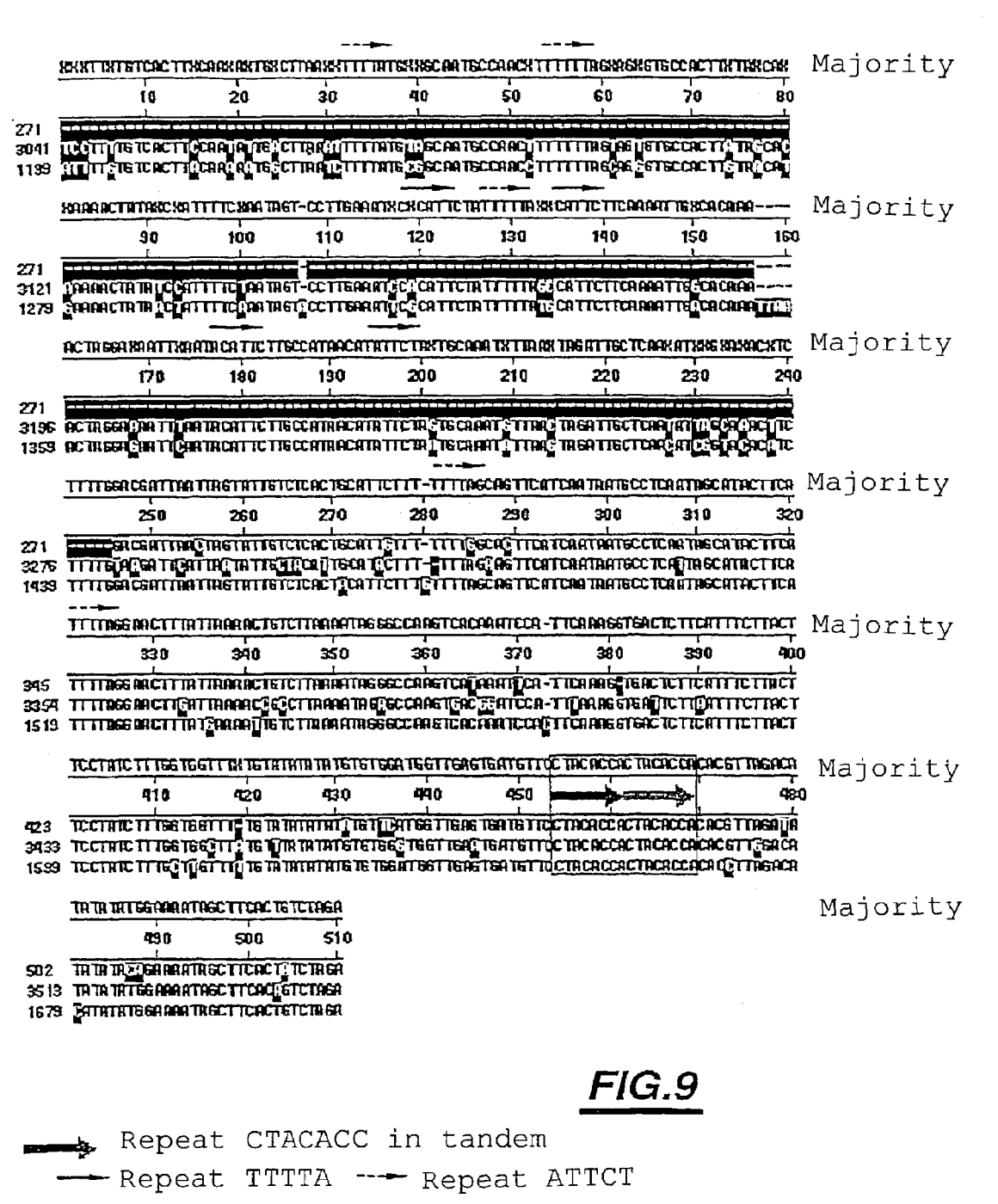

The presence of elements acting in cis is sought amongst the preserved sequences, the most remarkable being CTA-CACCA, in tandem just 50 bases upstream of the open reading phase (FIG. 9). This sequence is a good candidate for being an element responsible for a tissue-specific gene expression. The first of these repetitions is also placed in the loop of the greatest reversed repetition found in the three promoters. The sequences repeated more than twice are preserved only between the promoters pEsr2 and pEsr3, in the missing region of Esr1: for example the sequences ATTCT and TTTTA, each being repeated four times, a potential transcription enhancer in the light of the lowest expression of Esr1 (FIG. 9).

To demonstrate the functionality of the cis elements, constructs comprising deleted promoter nucleotide sequences, fused with GUS, were prepared.

By way of example, two techniques were used to create deletions of the promoter Esr2:
  by extensive digestion of 5' to 3' on the fragment Hind111-Xba1 by means of the Erase-a-base™ kit from Promega (constructions L140);
  by PCR amplification of fragments of the promoter (constructions L194).

The plasmids L190 and L194 contain deleted promoter Esr2 fused with a reporter gene Gus and a terminator in accordance with the techniques described in the following example.

For the transformation, the fragments containing the constructs, deleted promoters constructs Esr2-Gus-ter' were transferred into another plasmid containing the construct "promoter ubiquitin-luciferase-ter", the latter serving as an internal standard for quantifying the Gus activity and correcting the position effect of the insertion of the transgene in the genome on the expression, variable from one transformed plant to another.

The fragments of the promoter Esr2 resulting from these deletions are set out in the following table 1:

TABLE 1

| Chosen deletion technique | Remaining fragment of the promoter Esr2* |
|---|---|
| Digestion kit (L140) | 985–2493 |
|  | 1254–2493 |
|  | 1865–2493 |
|  | 1874–2493 |
|  | 1880–2493 |
|  | 2077–2493 |
| Amplification PCR (L194) | 2163–2493 |
|  | 2275–2493 |
|  | 2373–2493 |

*the numbering of the promoter Esr2 is based on the sequence pEsr2 presented in an annexe (SEQ ID NO: 2) which goes from HindIII (AAGCTT or A = position 1) to XbaI (TCTAGA or A = position 2493).

To demonstrate the functionality of the promoter nucleotide sequences described above, the inventors cloned them upstream of the reporter gene GUS and used the constructs obtained for the transformation of plants.

In a preferred manner, the deleted promoters Esr2 were obtained in accordance with the following protocols:

Firstly, deletions of 5' to 3' were effected using exonuclease III. The plasmid L124/19 containing the promoter of the gene Esr2 coupled to the gene of the β-glucuronidase described in Example 4.1 was digested by HindIII in order to generate an initiation site for the deletions and by PstI to create a protection site against the action of the exonuclease III. The deletions were carried out with the Erase-a-base™ (Promega) kit.

Secondly, fragments of the promoter were amplified using the initiator ESRX (5'GGGGTCTAGACTGTGAAGCTA TTTTCCA3' (SEQ ID NO: 8)) containing the restriction site XbaI (underlined) and ESRH1 (5'GGGGAAGCTTTACATT CTTGCCATAACATA3' (SEQ ID NO: 9)), ESRH2 (5'GG GGAAGCTTTTCATCAATAATGCCTCATT3' (SEQ ID NO: 10)) or ESRH3 (5'GGGGAAGCTTTAATTTCTTACT TCCTATCT3' (SEQ ID NO: 11)) containing the HindIII restriction site (underlined). The amplification products digested by XbaI and HindIII replaced the entire promoter Esr2 upstream of the gene of the β-glucuronidase in the plasmid L124/19.

The deleted promoters associated with the β-glucuronidase gene were then cloned in a plasmid containing the luciferase gene under the control of the promoter of the rice actin. The latter was obtained by cloning the fragment XhoI/NcoI of the plasmid pAct1-F4 (Mc Elroy D. et al., Mol Gen Genet., 231: 150–160, 1991) corresponding to the promoter and first intron of the rice actin, in a plasmid of the pGP214 type containing the luciferase gene and the terminator of nopaline synthase (Twell D. et al., Development 109, 705–713, 1990), digested by SalI/NcoI. An adaptor containing the restriction sites SalI and NotI, formed in nucleotides 5'GGCCAGTCGACAAAGCGGCCGCAT-GCA3' (SEQ ID NO: 12) and 5'TCAGCTGTTTCGCCG-GCGT3' (SEQ ID NO: 13) was introduced into the plasmid obtained, digested by NotI and PstI (plasmid L210). The fragments SalI/NotI containing the deleted promoters associated with the β-glucuronidase gene were cloned in the plasmid L210 digested by SalI and NotI.

Example 4

Preparation of Chimeric Constructs

All the constructions can be effected in particular according to the methods described in Sambrook et al. (1989). The adaptors which can be used by way of example for cloning these fragments upstream of the different effecting genes are described in the restriction maps of the corresponding plasmids.

4-1 GUS Chimeric Constructs

Figure 2:
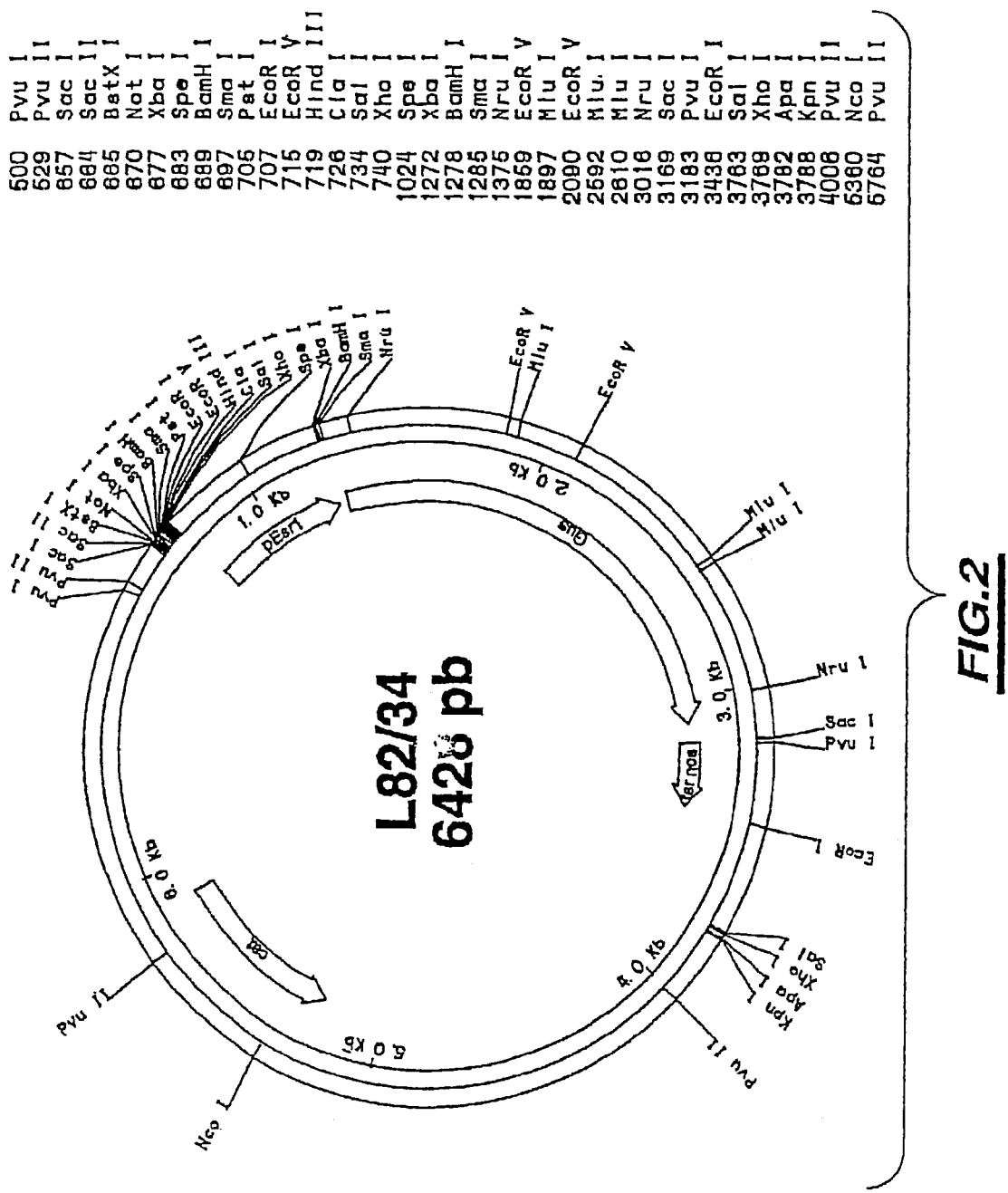
FIG. 2 depicts the restriction map of the plasmid L82/34, comprising in particular the promoter pEsr1 fused with Gus.

The plasmid L23/7 (Esr1) was deleted from a fragment SacI containing undesirable restriction sites. Then a fragment XbaI/EcoRI of 2164 pairs of bases of the plasmid pBI101 (Jefferson et al., 1987) containing a Gus gene (coding for the β-glucuronidase but with no promoter) and a terminating sequence nos, was introduced. The new plasmid thus formed was then digested by XhoI and the digestion product containing the promoter region associated with the Gus gene and positioned upstream of the latter was subcloned in the vector pBCKS+ (Stratagene) so that the promoter is close the hybridisation zone of the initiator T7, thus enabling the plasmid L82/34 to be obtained (FIG. 2, Table 2).

Figure 3:
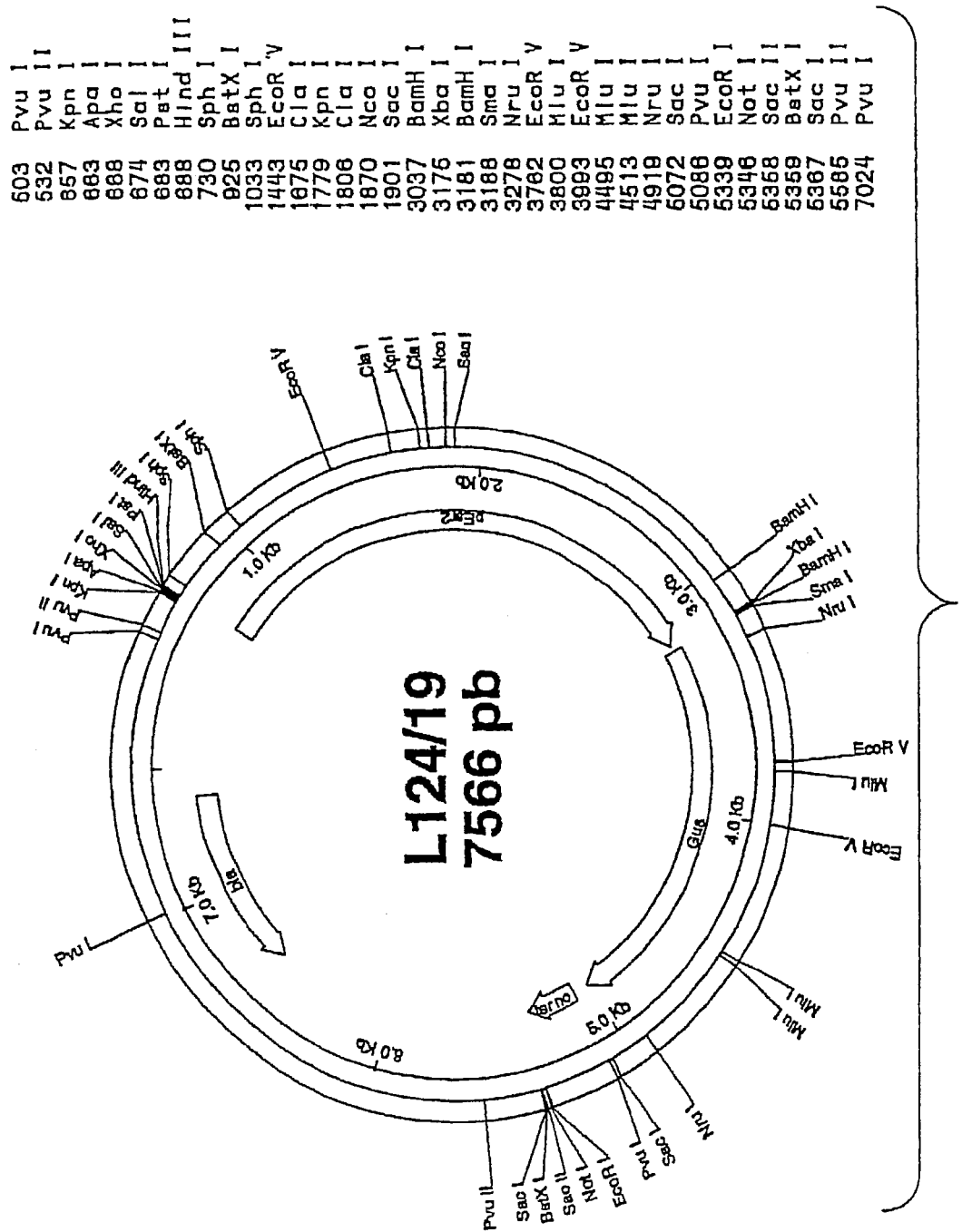
FIG. 3 depicts the restriction map of the plasmid L124.19, comprising in particular the promoter pEsr2 fused with Gus.
Figure 4:
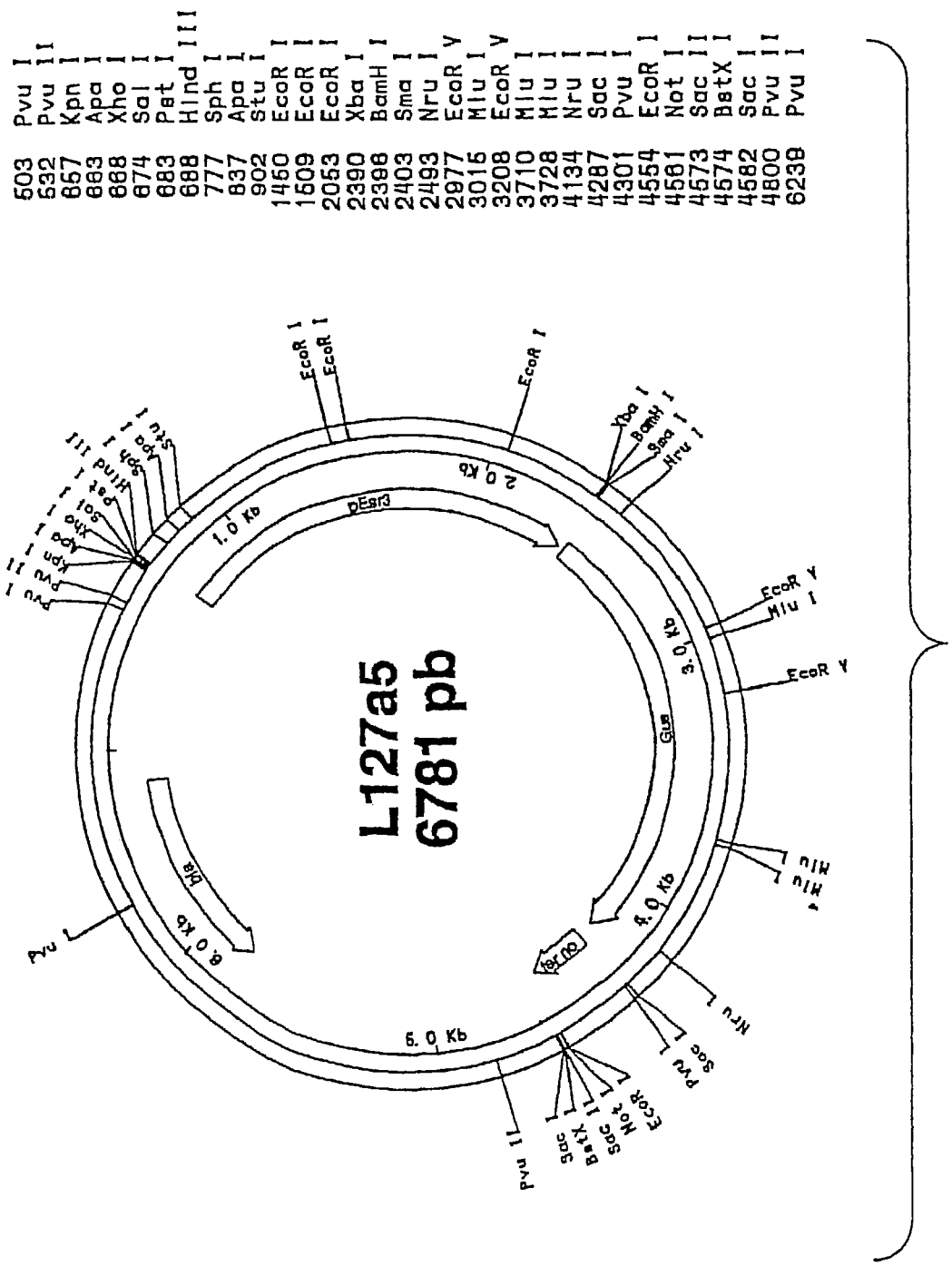
FIG. 4 depicts the restriction map of the plasmid L127a5, comprising in particular the promoter pEsr3 fused with Gus.

According to a similar protocol and with the restriction enzymes indicated in the corresponding figures, it was possible to obtain the plasmids L124/19 (pEsr2-GUS, FIG. 3, Table 3) and L127a5 (pEsr3-GUS, FIG. 4, Table 4).

It is also possible to use other reporter genes in replacement for GUS, for example GFP (Green Fluorescent Protein, Siemering K R et al., 1996), to confirm the results obtained with GUS.

According to a protocol similar to that described previously, the fragment HindIII-XbaI of the promoter pEsr2 was fused with the coding sequence for GFP.

TABLE 2

Characteristics of the plasmid L82/34

| Fragment | Position | Reference |
|---|---|---|
| pEsr1 | 741–1272 | |
| Gus | 1302–3107 | |
| ter nos | 3181–3434 | |
| cat | 5878–5223 | |
| pBCKS+ | 1–740 | Stratagene |
| L23/7 (pEsr1) | 741–1272 | Opsahl-Ferstad et al., 1997* and this example |
| pBI101 | 1273–3436 | Jefferson et al., 1987 |
| L23/7 | 3437–3763 | Opsahl-Ferstad et al., 1997 and this example |
| (upstream) | 3764–3769 | Stratagene |
| pBSSK+ | 3770–6428 | Stratagene |
| pBCKS+ | | |

*the insert corresponds to the fragment Esr1g1 drawn in FIG. 4 of Opsahl-Ferstad et al., 1997

TABLE 3

Characteristics of the plasmid L124/19

| Fragment | Position | Reference |
|---|---|---|
| pEsr2 | 689–3175 | |
| Gus | 3205–5010 | |
| ter nos | 5084–5337 | |
| bla | 7441–6584 | |
| pBSSK+ | 1–674 | Stratagene |
| Linker JFB 34 | 675–688 | this example[1] |
| L33/1 (pEsr2') | 689–3037 | this example** |
| L33/10 (pEsr2") | 3038–3175 | Opsahl-Ferstad et al., 1997 and this example** |
| pBI101 | 3176–5339 | Jefferson et al., 1987 |
| linker JFB56 | 5340–5346 | this example[2] |
| pBSSK+ | 5347–7566 | Stratagene |

**the inserts are presented partly as a fragment Esr2g1 in FIG. 4 of Opsahl-Ferstad et al., 1997
[1] adaptor JFB34: 5'TCGACTGCAGCCCA 3' (SEQ ID NO: 14)
3'GACGTCGGGTTCGA 5' (SEQ ID NO: 15)
[2] adaptor JFB56: 5'CTAGACCCGAATTCGC 3' (SEQ ID NO: 16)
3'TGGGCTTAAGCGCCGG 5' (SEQ ID NO: 17)

TABLE 4

Characteristics of the plasmid L127a5

| Fragment | Position | Reference |
|---|---|---|
| pEsr3 | 689–2390 | |
| Gus | 2420–4225 | |
| ter nos | 4229–4552 | |
| bla | 6656–5799 | |
| Pbssk+ | 1–674 | Stratagene |
| Linker JFB 34 | 675–688 | this example |
| L102c24 (pEsr3) | 689–2390 | this example |
| pBI101 | 2391–4554 | Jefferson et al., 1987 |
| linker JFB56 | 4555–4561 | this example |
| pBSSK+ | 4562–6781 | Stratagene |

4-2 Chimeric Constructs lpt

The lpt gene codes for isopentenyl-transferase, which is an enzyme involved in the synthesis of cytokinine, a phytohormone implicated in vegetable cell growth. The gene sequence was determined by Heidekamp F. et al. (1983). Prior works also showed that this sequence, under the control of a specific promoter of the ovule, made it possible to increase the dry matter content in the fruit, in tomatoes, Martineau B. et al. (1995).

Figure 5:
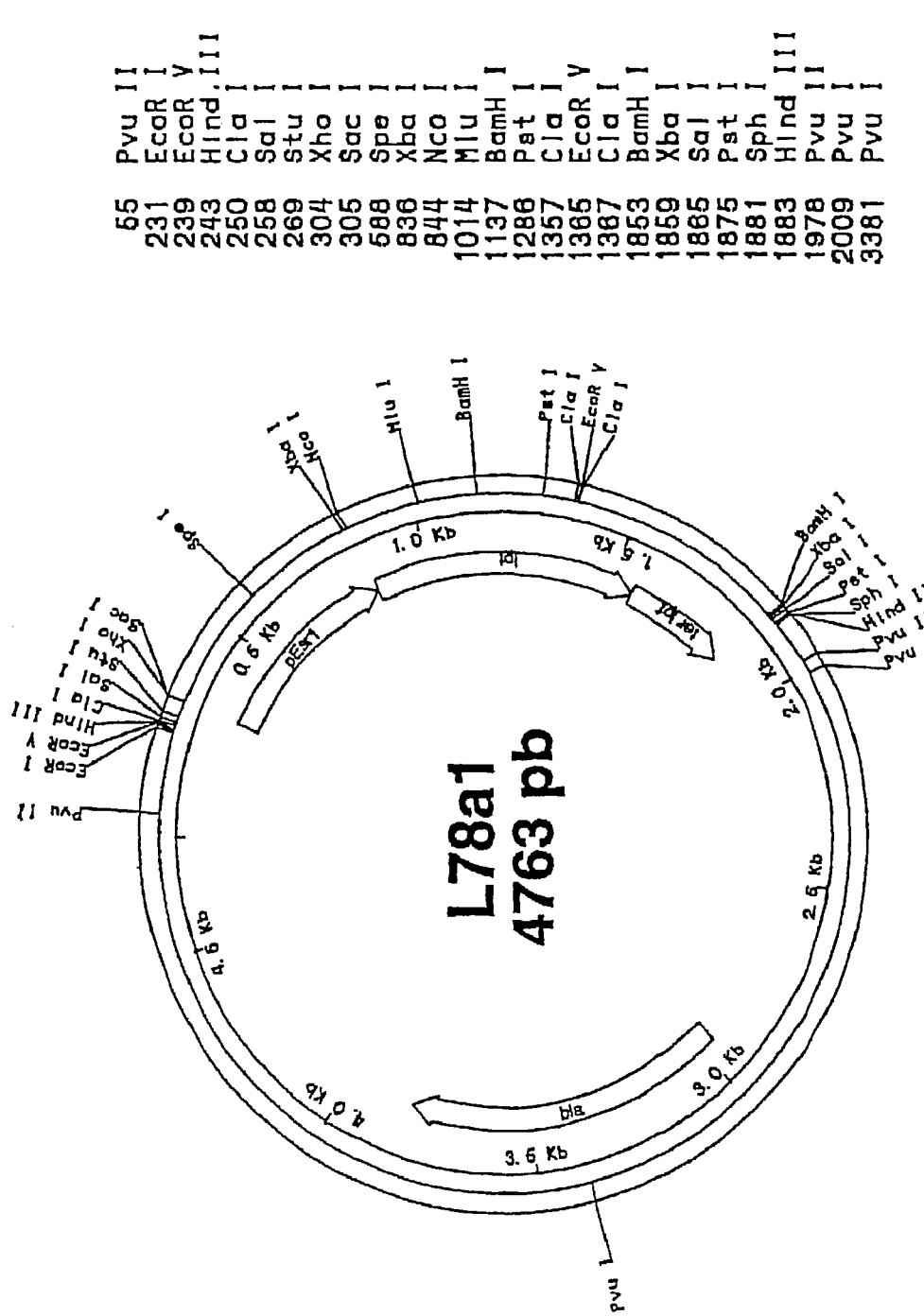
FIG. 5 depicts the restriction map of the plasmid L78a1, comprising in particular the promoter pEsr1 fused with lpt.
Figure 6:
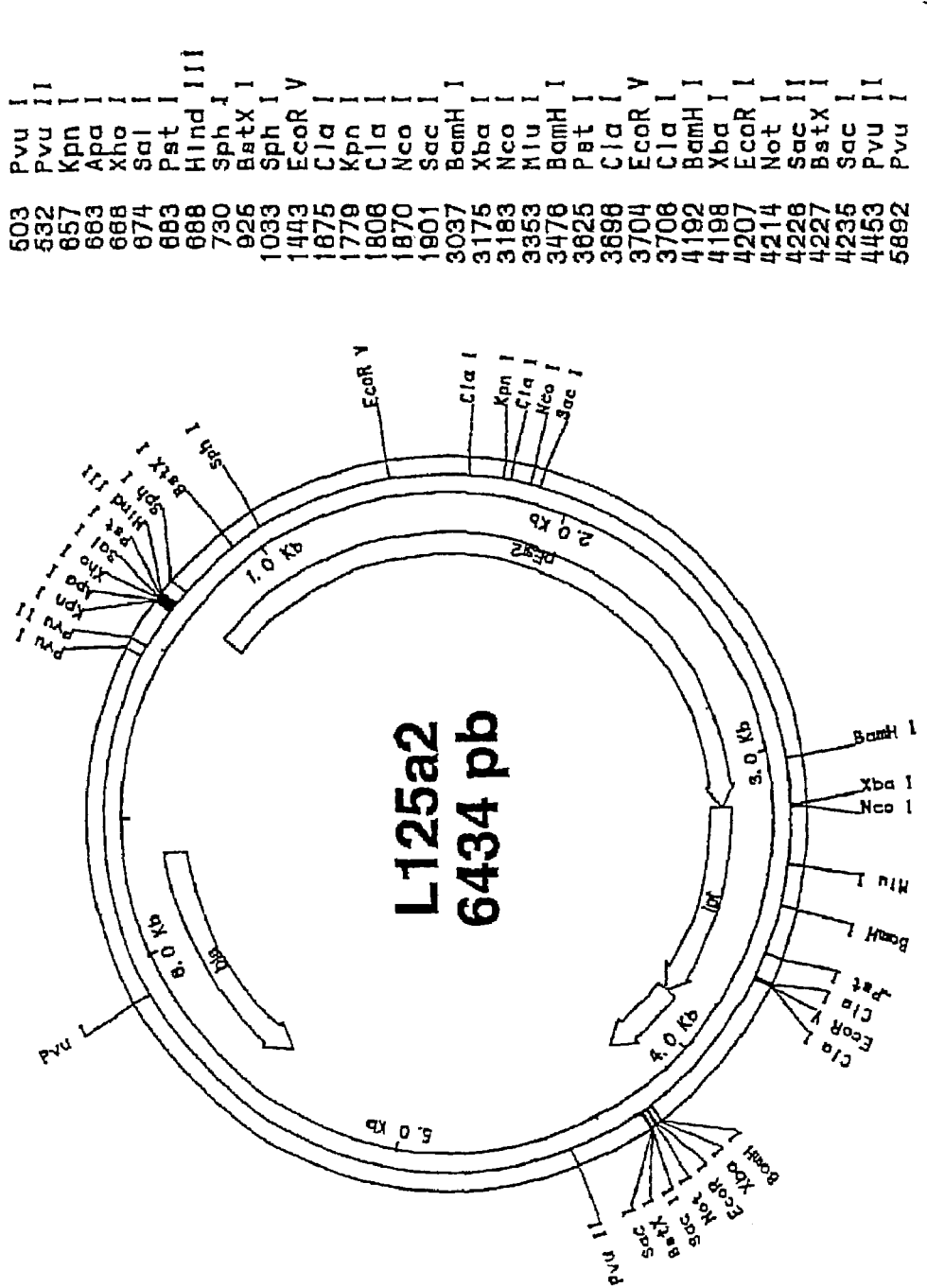
FIG. 6 depicts the restriction map of the plasmid L125a2, comprising in particular the promoter pEsr2 fused with lpt.

According to the cloning methods described above and with the fragments of nucleic acids and restriction enzymes indicated in the corresponding figures, it was possible to prepare constructs pEsr1-lpt (FIG. 5, Table 5) and pEsr2-lpt (FIG. 6, Table 6). It is also possible to obtain a construct pEsr3-lpt, according to the same protocol. For preparing these constructs, NcoI (CCATGG) sites straddling the codon ATG of the start of the open reading phase were used instead of the XbaI sites.

TABLE 5

Characteristics of the plasmid L78a1

| Fragment | Position | Reference |
|---|---|---|
| pEsr1 | 310–844 | |
| ipt | 846–1565 | |
| ter ipt | 1566– | |
| bla | 1850 | |
| | 2963–3823 | |
| pUC118 | 1–231 | Boebringer |
| L23/7 (pEsr1) | 232–844 | Opsahl-Ferstad et al., 1997 and this example |
| isolated mutation | 845 | Zhang et al., 1996 |
| pRZ1 | 846–1883 | Zhang et al., 1995 |
| pUC118 | 1884–4763 | Boehringer |

TABLE 6

Characteristics of the plasmid L125a2

| Fragment | Position | Reference |
|---|---|---|
| pEsr2 | 689–3183 | |
| ipt | 3185–3904 | |
| ter ipt | 3905–4189 | |
| bla | 6309–5449 | |
| pBSSK+ | 1–674 | Stratagene |
| Linker JFB 34 | 675–688 | this example |
| L33/1 (pEsr2') | 689–3037 | this example |
| L33/10 (pEsr2") | 3038–3183 | Opsahl-Ferstad et al., 1997 and this example |
| isolated mutation | 3184 | Zhang et al., 1996 |
| pRZ1 | 3185–4198 | Zhang et al., 1995 |
| adaptor JFB56 | 4199–4214 | this example |
| pBSSK+ | 4215–6434 | Stratagene |

4-3 Barnase Chimeric Constructs

The barnase gene codes for an Rnase. This gene was isolated using *Bacillus amyloliquefaciens* (Hartley, 1988). Its use for creating sterile male plants was described in the application EP 344 029 published by Mariani et al. (1990).

Figure 7:
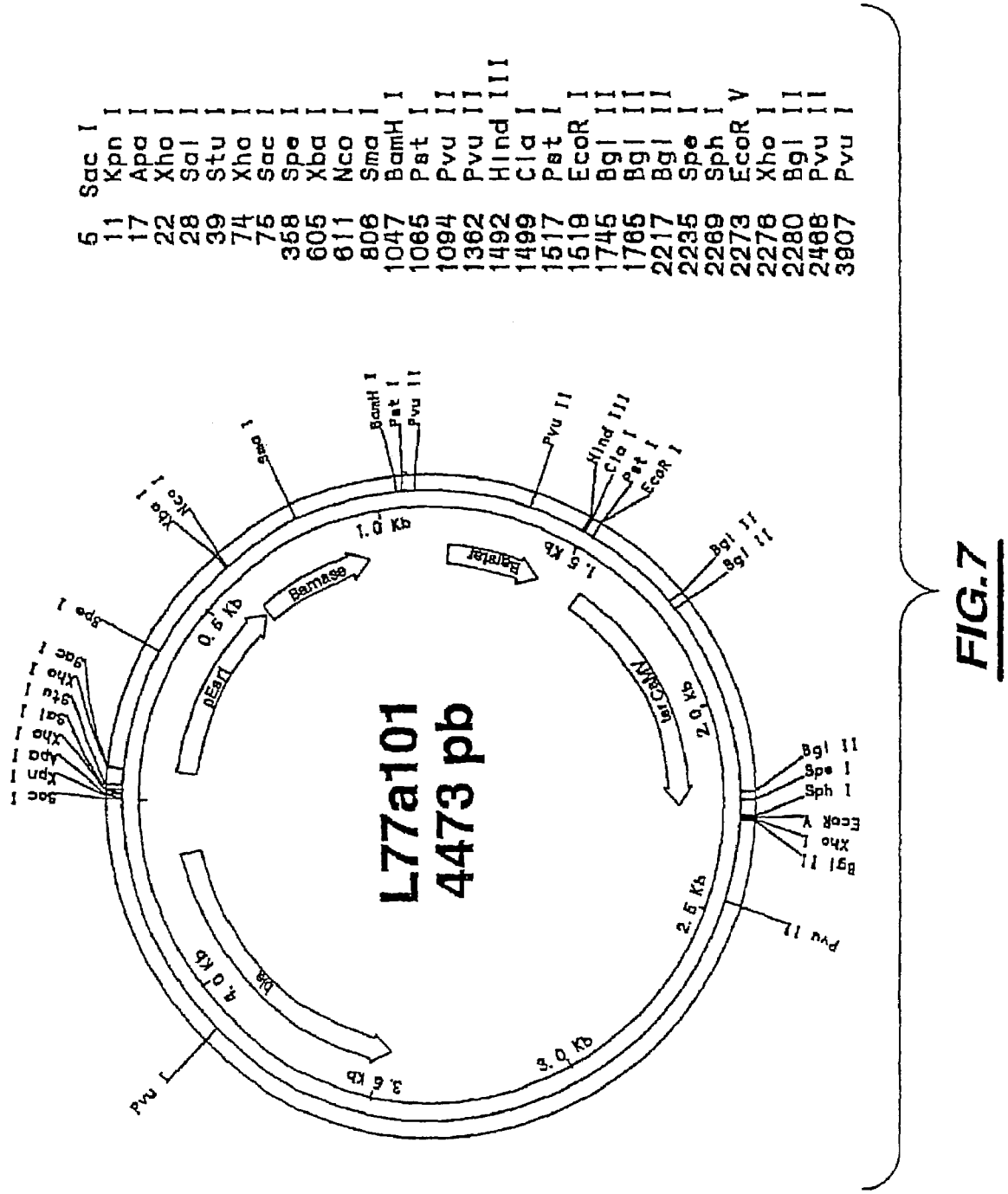
FIG. 7 depicts the restriction map of the plasmid L77a101, comprising in particular the promoter pEsr1 fused with Barnase.
Figure 8:
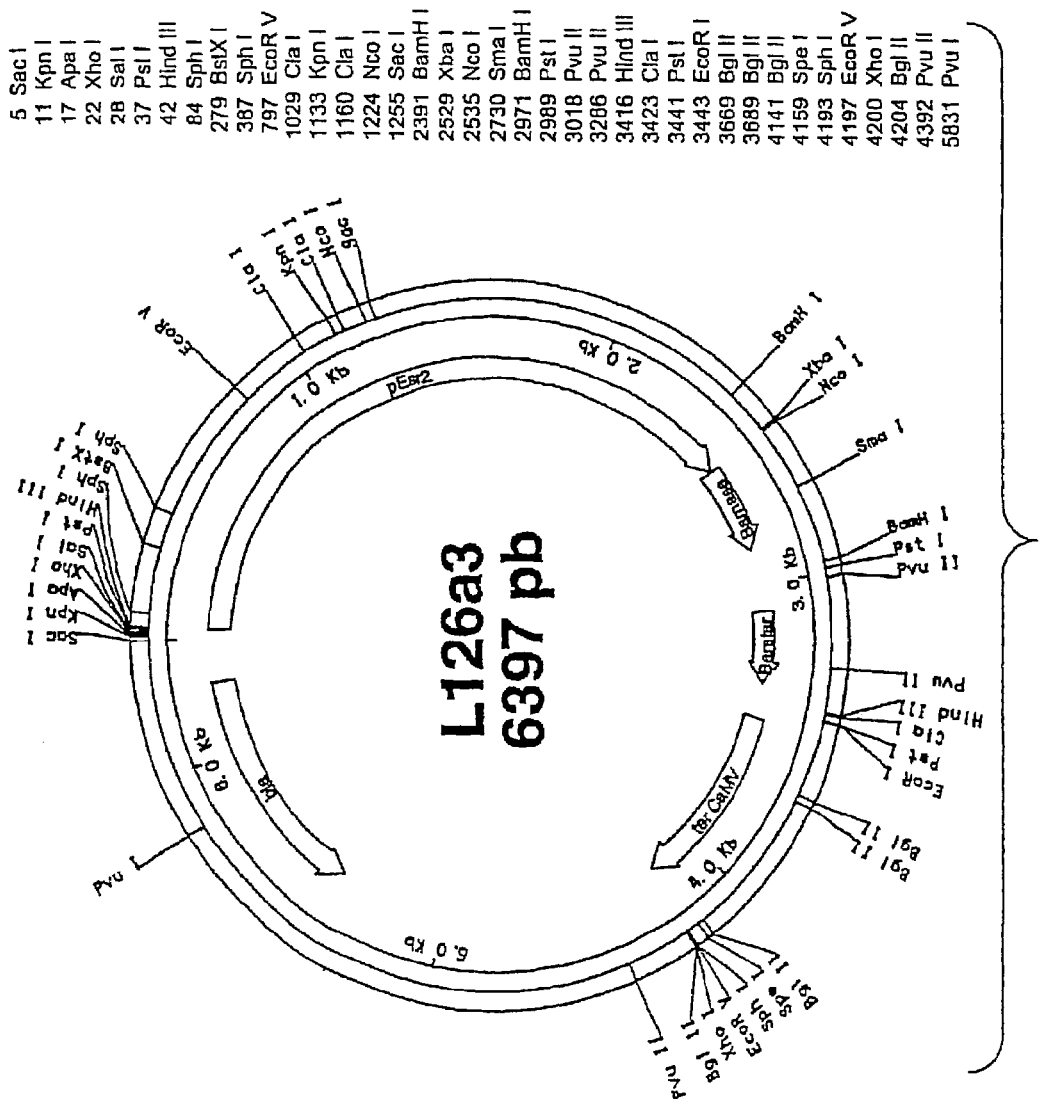
FIG. 8 depicts the restriction map of the plasmid L126a3, comprising in particular the promoter pEsr1 fused with Barnase.

In the context of the invention, the plasmids L77a101 (pEsr1-barnase) and L126a3 (pEsr2-barnase) described in FIGS. 7 (Table 7) and 8 (Table 8) were obtained from the plasmid "promoter A6-barnase" described in WO 92/11379, by replacing pA6 with the promoters pEsr1 and pEsr2 respectively, in accordance with the techniques known to persons skilled in the art.

It is also possible to obtain a construct pEsr3-Barnase, in accordance with a similar protocol.

TABLE 7

Characteristics of the plasmid L77a101

| Fragment | Position | Reference |
|---|---|---|
| pEsr1 | 80–605 | |
| Barnase | 613–945 | |
| ter CaMV | 1571–2257 | |
| bla | 4324–3467 | |
| pA3 | 1–28 | Scott et al., 1992 |
| L23/7 (pEsr1) | 29–605 | Opsahl-Ferstad et al., 1997 and this example |
| pA3 | 606–4473 | Scott et al., 1992 |

TABLE 8

Characteristics of the plasmid L126a3

| Fragment | Position | Reference |
|---|---|---|
| pEsr2 | 43–2529 | |
| Barnase | 2537–2869 | |
| ter CaMV | 3495–4181 | |
| bla | 6248–5391 | |
| pA3 | 1–28 | Scott et al., 1992 |
| linker JFB34 | 29–42 | this example |
| L33/1 (pEsr2') | 43–2391 | this example |
| L33/10 (pEsr2") | 2392–2529 | Opsahl-Ferstad et al., 1997 and this example |
| pA3 | 2530–6397 | Scott et al., 1992 |

4-4 Chimeric Construct antiEsr2

The reconstituted functional promoter Esr2 (2.49 kb), described in Example 2 and chosen preferentially in the light of the quantitative expression results described in Example 1, was fused with the sequence Esr2g2 (Opsahl et al., 1997) taken in antisense orientation, itself fused with the terminator Nos.

In a preferred manner, the chimeric construct containing the gene Esr2 in the reverse direction under the control of its own promoter was obtained in accordance with the following protocol:

In a plasmid derived from pJIT30 containing the promoter 35S, a multiple cloning site and the terminating sequence of the cabbage mosaic virus (Guerineau F. et al., Plant Mol Biol, 15: 127–136, 1990), an adaptor containing a SpeI site and formed by the oligonucleotides (5'GATCCACTAGTC-CCG (SEQ ID NO: 18)) and (5'AATTCGGGACTAGTG (SEQ ID NO: 19)) was inserted between the sites BamHI and EcoRI. The fragment EcoRI/SpeI of the plasmid L42 a14 (Opsahl-Ferstad et coll., 1997) was inserted in the plasmid described previously. The construction thus obtained contained the gene Esr2 in antisense orientation under the control of the promoter 35S (plasmid L79 b5).

Figure 11:
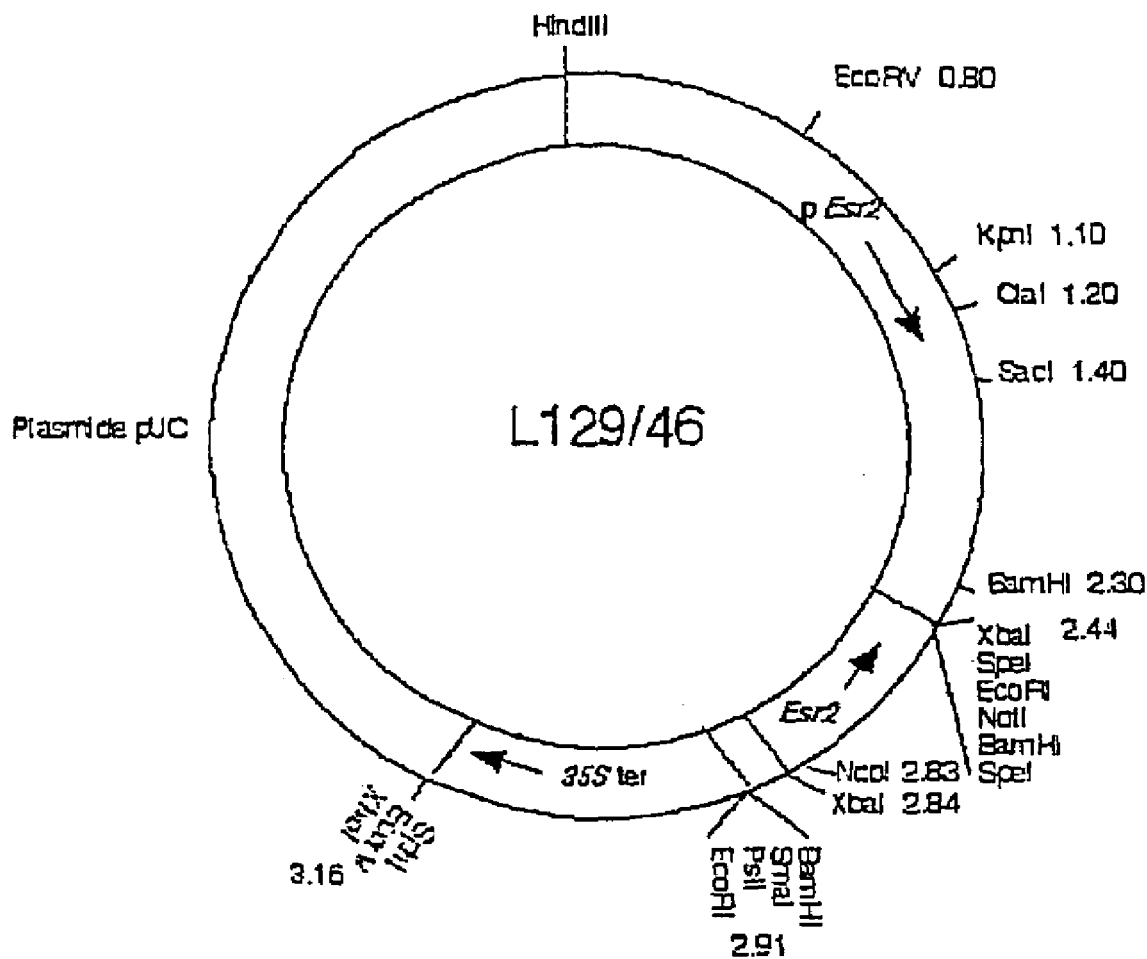
FIG. 11 depicts the restriction maps of the plasmid L129/46, comprising notably the promoter pEsr2 fused with the sequence Esr2 in antisense orientation.

The promoter 35S was eliminated in the plasmid L79 b5 by restriction by SacI and HindIII, and replaced by an adaptor containing the restriction site HindIII and NotI and formed by the oligonucleotides (5'AAGCTTTTTGCGGC-CGC (SEQ ID NO: 20)) and (5'TCGAGCGGCCG-CAAAAAGCTTAGCT (SEQ ID NO: 21)). The promoter Esr2 in the form of a fragment HindIII/NotI of 2.44 kb was introduced into this adaptor. The construction thus obtained contains the gene Esr2 in antisense orientation under the control of its own promoter (plasmid L129/46 (cf FIG. 11)).

According to a similar protocol, it is possible to obtain the constructs comprising the promoter Esr2 fused with the antisense sequences Esr1 and Esr3 respectively. It is also possible to obtain the same type of chimeric constructs with the other Esr promoters according to the invention.

Constructs comprising the constituent promoter 35S fused with the Esr antisense sequences described below have also been obtained.

Example 5

Obtaining Transgenic Plants (Necessity for the Stable Transformation of Maize)

Transient expression experiments using transformation by bombardment of vegetable cells, with chimeric constructs pEsr-GUS and constituent promoter-GUS respectively, did not give results revealing the specificity of expression of the promoters tested: no GUS activity was displayed in the area defined by the Esr cells. The small size of this area and other peculiar particularities could explain the fact that the technique is unsuited under standard conditions to transient expression. By way of example, the constituent promoters tested as a control are the rice actin promoters (McElroy et al., 1992), maize ubiquitin (Christensen et al., 1996), maize Adh (Dennis et al., 1984) and 35S (Odell et al., 1985), gave a blue colouring throughout the endosperm, demonstrating the functionality of the transformation system, but not in the area surrounding the embryo, which confirms the unsuitability of the system for this area.

The transformation aimed at a stable expression therefore became necessary for studying the specificity of expression of the promoters according to the invention.

5-1 Particle Gun

The method used is based on the use of a particle gun identical to the one described by J. Finer (1992). The target cells are undifferentiated cells in rapid divisions which have preserved suitability for the regeneration of entire plants. This type of cell composes the embryogenic callus (referred to as type II) of maize. These calluses are obtained from immature embryos of the genotype Hill according to the method and on the media described by Armstrong (Maize Handbook: 1994, M. Freeling, V. Walbot Eds, pp. 665–671). These fragments of the calluses with a surface area of 10 to 20 mm$^2$ were disposed, 4 hours before bombardment, at the rate of 16 fragments per dish, in the centre of a Petri dish containing a culture medium identical to the initiation medium, with 0.2 M of mannitol+0.2 M of sorbitol added. The plasmids described in the previous examples and carrying the genes to be introduced are purified on a Qiagen® column following the instructions of the manufacturer. They are then precipitated on particles of tungsten (M10) in accordance with the protocol described by Klein (1987). The particles thus coated are projected towards the target cells by means of the gun and in accordance with the protocol described by J. Finer (1992). The dishes of calluses thus bombarded are then sealed by means of Scellofrais® and then cultivated in darkness at 27° C. The first planting out took place 24 hours afterwards, and then every fortnight for 3 months on a medium identical to the initiation medium with a selective agent added. After 3 months or sometimes earlier, calluses are obtained whose growth is not inhibited by the selective agent, normally and for the major part composed of cells resulting from the division of a cell which integrated in its genotype one or more copies of the selection gene. The frequency of obtaining such calluses is approximately 0.8 callus per dish bombarded.

These calluses are identified, individualised, amplified and then cultivated so as to regenerate plant germs, modifying the hormonal and osmotic balance of the cells in accordance with the method described by Vain et al. (1989). These plants are then acclimatised in a greenhouse, where they can be crossed in order to obtain hybrids or self-fertilised.

5-2 Transformation by *Agrobacterium*

Another transformation technique which can be used in the context of the invention uses *Agrobacterium tumefaciens*, in accordance with the protocol described by Ishida et al. (1996), in particular from immature embryos from 10 days after fertilisation. All the media used are referenced in the reference cited. The transformation begins with a co-culture phase in which the immature embryos of the maize plants are brought into contact for at least 5 minutes with *Agrobacterium tumefaciens* LBA 4404 containing the superbinary vectors. The superbinary plasmid is the result of a homologous recombination between an intermediate vector carrying ADN-T containing the gene of interest and/or the selection marker derived from the plasmids described in the previous examples, and the vector pSB1 of Japan Tobacco (EP 672 752) which contains: the genes virB and virG of the plasmid pTiBo542 present in the supervirulent strain A281 of *Agrobacterium tumefaciens* (ATCC 37349) and a homologous region found in the intermediate vector allowing this homologous recombination. The embryos are then placed on a medium LSAs for 3 days in darkness and at 25° C. A first selection is effected on the transformed calluses. The embroygenic calluses are transferred onto a medium LSD5 containing phosphinotricine at 5 mg/l and cefotaxime at 250 mg/l (elimination or limitation of the contamination by *Agrobacterium tumefaciens*). This step is carried out 2 weeks in darkness and at 25° C. The second selection step is carried out by the transfer of the embryos which are developed on an LSD5 medium, on an LSD10 medium (phosphinotricine at 10 mg/l) in the presence of cefotaxime, for 3 weeks under the same conditions as before. The third selection step consists of excising the type I calluses (fragments of 1 to 2 mm) and transferring them 3 weeks in darkness and at 25° C. onto an LSD 10 medium in the presence of cefotaxime.

The regeneration of the plant germs is carried out by excising the type I calluses which have proliferated and transferring them onto an LSZ medium in the presence of phosphinotricine at 5 mg/l and cefotaxime for 2 weeks at 22° C. and under continuous light.

The plant germs which have regenerated are transferred onto an RM+G2 medium containing 100 mg/l of Augmentin for 2 weeks at 22° C. and under continuous illumination for the development step. The plants obtained are then transferred to the phytotron with a view to their acclimatisation.

5-3 Preferred Mode for the Barnase Constructs: Retransformation of the Act-barstar Calluses The barnase chimeric constructs described in Example 3 can be used for conventional transformations according to one or other of the techniques described above.

According to a preferred mode, adapted to the toxic character of barnase, pretransformed calluses are used for the transformation, containing the gene barstar, which codes for a specific inhibitor of Barnase (Hartley, 1988). This gene serves as "protection" during the process of regenerating these calluses, which takes place essentially from embryogenesis in maize.

Step a: Obtaining a Line Expressing Barstar and a Plasmid Containing the Gene for Resistance to Hygromycine:

A first transformation step is carried out in accordance with one of the protocols described, with the plasmid pWP280 containing the cassette pActin-intron-Barstar-Nos poly A.

This cassette was obtained according to the following steps: the barnase fragment was amplified with PCR from the plasmid pTG2 (Horovitz et al., 1990) and then subcloned as a fragment XbaI/HindIII in the plasmid pBluescript KS+ (Stratagene) giving the plasmid pWP118.

The barstar gene was then transferred as a fragment XbaI/HincII into a site XbaI/SmaI of the plasmid pW90, derived from the plasmid pJIT30 described by Guerineau et al. (1990) (promoter 35SCaMV replaced by the double promoter 35S and the polylinker region between the sites XbaI and EcoRI replaced by the sites SpeI, BamHI, SmaI and PstI).

Figure 10:
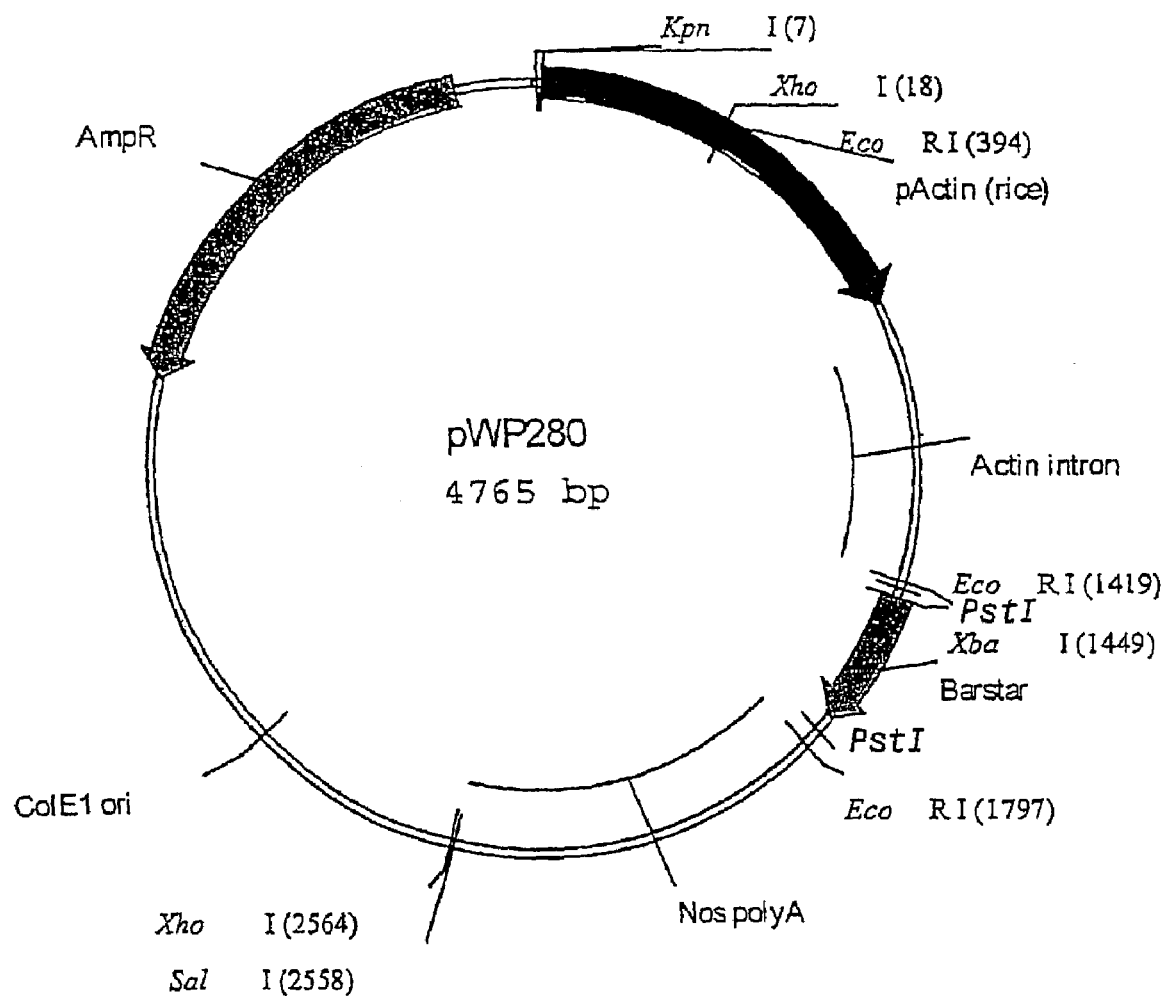
FIG. 10 depicts the restriction map of the plasmid pWP280.

The region polyA CaMV of the plasmid obtained is replaced by the region nos polyA of pED23 (Dale et al., 1991) forming the plasmid pWP266. Finally, the double promoter region 35S CaMV is replaced by the rice actin promoter and the intron derived from pCOR113 (Mc Elroy et al., 1991) forming the plasmid pWP280 (FIG. 10).

The "actin-barstar promoter" plants thus produced are analysed by Northern Blot in order to identify the plants correctly expressing ARNm coding for Barstar. The plants thus produced supply embryos expressing the Barstar gene, which will be used for producing type II calluses according to known techniques: putting the embryos in culture on a medium inducing callogenesis and replanting on a selective medium containing hygromycin.

Step b: Transformation of These Calluses with the Barnase Chimeric Construct:

The act-barstar calluses obtained at the previous step are then bombarded according to the technique described at point 5-1 with the "Esr-barnase promoter" construct previously described with a plasmid conferring resistance to Basta (pDM302, Mc Elroy et al., 1991). The two genes are then separated into the descendants by segregation, in order to see the effect of the single promoter construct Esr-barnase.

Better results, particularly with regard to the effectiveness of transformation and the number of plants regenerated, were obtained according to this preferred mode, in comparison with the conventional technique which aims to transform the calluses directly by means of the "Esr-barnase" constructs.

Example 6

Demonstration of the Functionality of the Promoter Sequences (the Case of GUS Constructs)

In order to detect the β-glucuronidase activity, the maize seeds issuing from plants transformed by the particle gun are harvested at precise stages of the development and cut along the longitudinal axis. They are incubated in the presence of 5-bromo-4-chloro-3-indolyl-β-D-glucuronic acid (X-GlcA, Duchefa), at 37° C. for 24 hours (Jefferson et al., 1987).

In the case of the construct Esr2-Gus in particular, the blue colouring is delimited at the contour of the embryo at the 4$^{th}$ and 5$^{th}$ days after pollination, and then only at the suspensor level on the 6$^{th}$ and 7$^{th}$ days, and finally at the base of the suspensor at days 9, 12, 13 and 15.

The expression results in the transgenic plants demonstrate that the fragments 5' described in the present invention correspond to functional promoters and that they are sufficient for a correct spatio-temporal expression, in accordance with the prior results of Opsahl et al. (1997).

The use of these promoter nucleotide sequences in molecular constructions intended to improve the agronomic, food or industrial quality of a plant is particularly advantageous for modifying the size of the embryo or of the endosperm and/or its development.

BIBLIOGRAPHY

Armstrong (1994), *Maize Handbook*, Freeling, M., Walbot, V. Eds, 665–671.
Barloy, D. et coll. (1989), *Maydica*, 34, 303–308.
Becker, H. A. et al. (1999), *Domains of gene expression in developing endosperm*, 361–375.
Breton, C. et al. (1995), *Plant Mol. Biol.*, 27, 105–113.
Christensen et al. (1996), *Transgenic Res.*, 5: 213.
Clark, J. K. and Sheridan, W. F. (1986), *J. Heredity*, 77, 83–92.
Dale et al. (1990), *Gene*, 91: 79–85.
Davis, R. W. et coll. (1990), *Can. J. Bot.*, 68, 471–479.
Dennis (1884), *Nucl. Ac. Res.*, 12: 3983–4000.
Devic et al. (1997), *Plant Physiol. Biochem.*, 35: 35(4): 331–339.
Finer, J. (1992), *Plant Cell Report*, 11: 323–328.
Gerdes, J. T. and Tracy, W. F. (1993), *Crop Sci.*, 33, 334–337.
Guerche et al. (1987), *Mol. Gen. Genet.*, 206: 382.
Guerineau et al. (1990), *Plant. Mol. Biol.*, 15: 127–136.
Hartley et al. (1988), *J. Mol. Biol.*, 202, 913–915.
Heidekamp, F. et al. (1983), *Nucl Acids Res*, 11, 6211–6223.
Horovitz et al. (1990), *J. Mol. Biol.*, 216: 1031–1044.
Hu et al. (1995), *Molecular and General Genetics*, 248: 471–480.
Hueros, G. et al. (1995), *Plant Cell*, 7, 747–757.
Ishida et al. (1996), *Nature Biotechnology*, 14: 745–750.
Jefferson et al. (1987), *Plant Molecular Biology Reporter*, 5(4): 387–405.
Klein (1987), *Nature*, 327: 70–73.
Kowles, R. V. and Phillips, R. L. (1988), *Int. Rev. Cytol.*, 112, 97–136.
Kyle, D. J. and Styles, E. D. (1977), *Planta*, 137, 185–193.
Liang, P. and Pardee, A. B. (1992), *Science*, 257, 967–971.
Lopes, M. A. and Larkins, B. A. (1993), *Plant Cell*, 5, 1383–1399.
Mariani et al. (1990), *Nature*, 347, 737–741.
Mc Elroy et al. (1991), *Mol. Gen. Genet.*, 231: 150–160.
McElroy et al., *Plant Cell*, 2: 163–171, 1990.
Odell et al. (1985), *Nature*, 313: 810–812.
Opsahl-Ferstad, H. D. et al. (1997), *The Plant J.*, 12, 235–246.
Poole et al. (1985), *Cell*, 40: 37–43.
Sambrook et al. (1989), *Molecular Cloning—A laboratory manual*, Cold Spring Harbor Laboratory Press.
Schel, J. H. N. et coll. (1984), *Can. J. Bot.*, 62, 2842–2856.
Scott et al. (1992), patent application WO 92/11 379.
Siemering, K. R. et al. (1996), *Current Biology*, 6, 1653–1663.
Twell, D. et al., *Development*, 109, 705–713, 1990.
Vain et al. (1989), *Plant Cell Tissue and Organ Culture*, 18: 143–151.
Xu, J. et al. (1995), *Plant Physiol.*, 108, 1293–1294.
Zhang et al. (1995), The effect of auxin on cytokinin levels and metabolism in transgenic tobacco tissue an ipt gene, *Planta*, 196: 84–94.
Zhang et al. (1996), Expression of the isopentenyl transferase gene is regulated by auxin in transgenic tobacco tissues, *Transgenic Res.*, 5: 57–65.

---

The invention claimed is:

1. An isolated promoter nucleotide sequence allowing an expression of the coding sequences to which it is operatively bound, said expression being i) specific to the region of an endosperm surrounding an embryo in seeds of angiosperms and ii) intervening in the early stages of development of the endosperm, wherein said promoter sequence comprises SEQ ID NO: 2.

2. An expression cassette comprising a promoter nucleotide sequence allowing an expression of the coding sequences to which said promoter sequence is operatively bound, said expression being i) specific to the region of the endosperm surrounding an embryo in seeds of angiosperms and ii) intervening in the early stages of development of the endosperm, wherein said promoter sequence comprises SEQ ID NO: 2,
the promoter nucleotide sequence being operatively bound to at least one gene of interest.

3. The expression cassette according to claim 2, in which the gene of interest codes for a protein which is selected from the group consisting of a protein involved in the development of the embryo, the development of the endosperm, the cell growth, the metabolism of sugars, the metabolism of fatty acids, the metabolism of a toxic protein and the metabolism of a transcription inhibiting protein.

4. The expression cassette according to claim 2, in which the gene of interest codes for a first protein which is selected from the group consisting of barnase and isopentenyltransferase.

5. An expression vector containing an expression cassette comprising promoter nucleotide sequence allowing an expression of the coding sequences to which said promoter nucleotide sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2,
the promoter nucleotide sequence being operatively bound to at least one gene of interest.

6. An angiosperm plant host cell, transformed by an expression vector containing an expression cassette comprising promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2,
the promoter nucleotide sequence being operatively bound to at least one gene of interest.

7. An angiosperm plant host cell in the form of cereal transformed by an expression vector containing an expression cassette comprising an isolated promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2,
the promoter nucleotide sequence being operatively bound to at least one gene of interest.

8. A transgenic plant, generated from an angiosperm plant host cell, transformed by an expression vector containing an expression cassette comprising an isolated promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest.

9. A part of a transgenic plant, selected from the group consisting of fruit, seed, grain and pollen, generated from an angiosperm plant host cell, transformed by an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest.

10. A transgenic plant, generated from an angiosperm plant host cell, transformed by an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in particular in the early stages of development of the endosperm, wherein said promoter sequence comprises SEQ ID NO: 2, the promoter nucleotide sequence being operatively bound to at least one gene of interest, wherein the transgenic plant is a plant selected from the group consisting of a cereal, an oily plant, maize, wheat, rape and sunflower.

11. A part of a transgenic plant selected from the group consisting of fruit, seed, grain and pollen, generated from an angiosperm plant host cell, transformed by an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest, wherein the transgenic plant is a plant selected from the group consisting of a cereal, an oily plant, maize, wheat, rape and sunflower.

12. A hybrid transgenic plant obtained by crossing parts of transgenic plants, each part of the transgenic plant being selected from the group consisting of fruit, seed, grain and pollen, generated from an angiosperm plant host cell, transformed by an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest.

13. A hybrid transgenic plant obtained by crossing transgenic plants, generated from an angiosperm plant host cell, transformed by an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest, wherein the transgenic plant is a plant selected from the group selected from a cereal, an oily plant, maize, wheat, rape and sunflower.

14. A method of obtaining an angiosperm plant having improved agronomic or nutritional qualities, comprising the steps consisting of:

transforming at least one angiosperm plant cell by means of an expression vector containing an expression cassette comprising a promoter nucleotide sequence allowing an expression of the coding sequences to which said promoter sequence is operatively bound, said expression being i) specific to the region of an endosperm surrounding an embryo in seeds of angiosperms and ii) intervening in the early stages of development of the endosperm, wherein said promoter sequence comprises SEQ ID NO: 2, the promoter nucleotide sequence being operatively bound to at least one gene of interest; and cultivating the cell thus transformed so as to generate a plant containing in its genome an expression cassette comprising a promoter nucleotide sequence allowing an expression of the coding sequences to which said promoter sequence is operatively bound, said expression being i) specific to the region of the endosperm surrounding the embryo in the seeds of the angiosperms and ii) intervening in the early stages of development of the endosperm, wherein said promoter sequence comprises SEQ ID NO: 2, the promoter nucleotide sequence being operatively bound to at least one gene of interest.

* * * * *